(12) United States Patent
Weinschenk et al.

(10) Patent No.: US 11,988,669 B2
(45) Date of Patent: *May 21, 2024

(54) METHOD FOR THE ABSOLUTE QUANTIFICATION OF NATURALLY PROCESSED HLA-RESTRICTED CANCER PEPTIDES

(71) Applicant: Immatics Biotechnologies GmbH, Tuebingen (DE)

(72) Inventors: Toni Weinschenk, Aichwald (DE); Julia Leibold, Tuebingen (DE)

(73) Assignee: Immatics Biotechnologies GmbH (DE)

( * ) Notice: Subject to any disclaimer, the term of this patent is extended or adjusted under 35 U.S.C. 154(b) by 1199 days.

This patent is subject to a terminal disclaimer.

(21) Appl. No.: 16/685,765

(22) Filed: Nov. 15, 2019

(65) Prior Publication Data
US 2020/0103408 A1   Apr. 2, 2020

Related U.S. Application Data

(63) Continuation of application No. 14/969,423, filed on Dec. 15, 2015, now Pat. No. 10,545,154.

(60) Provisional application No. 62/097,994, filed on Dec. 30, 2014.

(30) Foreign Application Priority Data

Dec. 30, 2014   (GB) ..................... 1423361

(51) Int. Cl.
*G01N 33/68* (2006.01)
*A61K 39/00* (2006.01)
*G01N 33/569* (2006.01)
*C07K 14/74* (2006.01)

(52) U.S. Cl.
CPC ... *G01N 33/6848* (2013.01); *G01N 33/56977* (2013.01); *G01N 33/6842* (2013.01); *G01N 33/6878* (2013.01); *G01N 2333/70539* (2013.01); *G01N 2458/15* (2013.01); *G01N 2496/00* (2013.01); *G01N 2560/00* (2013.01); *G01N 2570/00* (2013.01)

(58) Field of Classification Search
None
See application file for complete search history.

(56) References Cited

U.S. PATENT DOCUMENTS

| | | | |
|---|---|---|---|
| 7,811,828 B2 | 10/2010 | Lemmel et al. | |
| 9,783,849 B2 * | 10/2017 | Weinschenk | C07K 14/4748 |
| 9,791,443 B2 * | 10/2017 | Weinschenk | G01N 33/6848 |
| 9,791,444 B2 * | 10/2017 | Weinschenk | G01N 33/56977 |
| 10,077,171 B2 * | 9/2018 | Chustz | B66C 15/06 |
| 10,227,381 B2 * | 3/2019 | Weinschenk | A61P 13/08 |
| 10,420,816 B1 * | 9/2019 | Fritsche | A61K 39/0011 |
| 10,478,471 B2 * | 11/2019 | Fritsche | A61K 38/39 |
| 10,526,407 B2 * | 1/2020 | Alten | A61K 45/06 |
| 10,545,154 B2 * | 1/2020 | Weinschenk | G01N 33/6878 |
| 10,889,645 B2 * | 1/2021 | Unverdorben | C07K 14/7051 |
| 2011/0257890 A1 | 10/2011 | Weinschenk et al. | |
| 2013/0045191 A1 * | 2/2013 | Weinschenk | A61K 38/39 |
| | | | 435/69.3 |
| 2013/0096016 A1 | 4/2013 | Weinschenk et al. | |

FOREIGN PATENT DOCUMENTS

| | | |
|---|---|---|
| EP | 1420245 A2 | 5/2004 |
| EP | 1508047 A2 | 2/2005 |
| WO | 03025576 A2 | 3/2003 |
| WO | 03100432 A2 | 12/2003 |
| WO | 2005076009 A2 | 8/2005 |
| WO | 2011128448 A1 | 10/2011 |
| WO | 2012140429 A2 | 10/2012 |
| WO | 2012178030 A2 | 12/2012 |

OTHER PUBLICATIONS

Sykulev et al (Immunity, 1996, 4: 565-571) (Year: 1996).*
Rammensee et al (Immunol. Rev. 2002, 188: 164-176) (Year: 2002).*
Montes et al (Clin. Exp. Immunol. 2005, 142: 292-302) (Year: 2005).*
Anderson et al. (J. Proteome. Res., 2012, 11: 1868-1878) (Year: 2012).
Bozzacco et al. ( J. Proteome Res. 2011 , 10( 11): 5016-5030) (Year: 2011).
Kalandadze et al. (JBC, 1998, 271 (33): 20156-20162) (Year: 1998).
Rammensee et al. (Immunological Rev. 2002, 188: 164-176) (Year: 2002).
Hassan Chopie et al.; "Accurate quantitation of MHC-bound peptides by application of isotopically labeled peptide MHC complexes"; Journal of Proteomics; vol. 109, Jul. 19, 2014; pp. 240-244; XP029080675.
Susann Muller et al.; "Functional single-cell analyses: flow cytometry and cell sorting of microbial populations tmd communities"; FEMS Microbiology Reviews; vol. 34, No. 4, Jul. 1, 2010; pp. 554-587; XP055253409.
International Search Report dated Mar. 23, 2016, for PCT/EP2015/079873.

(Continued)

*Primary Examiner* — Michael Szperka
*Assistant Examiner* — Marianne Dibrino
(74) *Attorney, Agent, or Firm* — McBee Moore & Vanik IP, LLC

(57) ABSTRACT

The present invention relates to a method for the absolute quantification of naturally processed HLA-restricted cancer peptides, i.e. the determination of the copy number of peptide(s) as presented per cell. The present invention can not only be used for the development of antibody therapies or peptide vaccines, but is also highly valuable for a molecularly defined immuno-monitoring, and useful in the processes of identifying of new peptide antigens for immunotherapeutic strategies, such as respective vaccines, antibody-based therapies or adoptive T-cell transfer approaches in cancer, infectious and/or autoimmune diseases.

16 Claims, 17 Drawing Sheets
(17 of 17 Drawing Sheet(s) Filed in Color)
Specification includes a Sequence Listing.

(56) References Cited

OTHER PUBLICATIONS

Great Britain Search Report dated Sep. 29, 2015, for GB 1423361.3.
D. Lebert et al.; "Production and Use of Stable Isotope-Labelled Proteins for Absolute Quantitative Proteomics"; MEthods in Molecular Biology; 2011; vol. 753; pp. 93-116.
Moritz et al., "Approaches for the quantification of protein concentration ratios." Proteomics (2003) 3(11), 2208-2220.
Fortier et al., "The MHC class I peptide repertoire is molded by the transcriptome." The Journal of Experimental Medicine (2008) 205(3), 595-610.
Singh-Jasuja et al., "The Ti.ibingen approach: identification, selection, and validation of tumor-associated HLA Deptides for cancer therapy." Cancer Immunology Immunotherapy (2004) 53(3), 187-195.

* cited by examiner

SEQUENCE LISTING

```
<160> NUMBER OF SEQ ID NOS: 25

<210> SEQ ID NO 1
<211> LENGTH: 9
<212> TYPE: PRT
<213> ORGANISM: Homo sapiens

<400> SEQUENCE: 1

Lys Ile Gln Glu Ile Leu Thr Gln Val
1               5

<210> SEQ ID NO 2
<211> LENGTH: 9
<212> TYPE: PRT
<213> ORGANISM: Homo sapiens

<400> SEQUENCE: 2

Tyr Val Tyr Gln Asn Asn Ile Tyr Leu
1               5

<210> SEQ ID NO 3
<211> LENGTH: 9
<212> TYPE: PRT
<213> ORGANISM: Homo sapiens

<400> SEQUENCE: 3

Phe Leu Val Asp Gly Ser Trp Ser Val
1               5

<210> SEQ ID NO 4
<211> LENGTH: 9
<212> TYPE: PRT
<213> ORGANISM: Homo sapiens

<400> SEQUENCE: 4

Thr Leu Ser Ser Ile Lys Val Glu Val
1               5

<210> SEQ ID NO 5
<211> LENGTH: 9
<212> TYPE: PRT
<213> ORGANISM: Homo sapiens

<400> SEQUENCE: 5

Tyr Leu Leu Ser Tyr Ile Gln Ser Ile
1               5

<210> SEQ ID NO 6
<211> LENGTH: 9
<212> TYPE: PRT
<213> ORGANISM: Homo sapiens

<400> SEQUENCE: 6
```

Phe Leu Leu Asp Gly Ser Ala Asn Val
1               5

<210> SEQ ID NO 7
<211> LENGTH: 9
<212> TYPE: PRT
<213> ORGANISM: Homo sapiens

<400> SEQUENCE: 7

Ala Met Ser Ser Lys Phe Phe Leu Val
1               5

<210> SEQ ID NO 8
<211> LENGTH: 9
<212> TYPE: PRT
<213> ORGANISM: Homo sapiens

<400> SEQUENCE: 8

Thr Leu Asp Pro Arg Ser Phe Leu Leu
1               5

<210> SEQ ID NO 9
<211> LENGTH: 9
<212> TYPE: PRT
<213> ORGANISM: Homo sapiens

<400> SEQUENCE: 9

Ala Leu Asp Gly Phe Val Met Val Leu
1               5

<210> SEQ ID NO 10
<211> LENGTH: 9
<212> TYPE: PRT
<213> ORGANISM: Homo sapiens

<400> SEQUENCE: 10

Tyr Val Asp Pro Val Ile Thr Ser Ile
1               5

<210> SEQ ID NO 11
<211> LENGTH: 9
<212> TYPE: PRT
<213> ORGANISM: Homo sapiens

<400> SEQUENCE: 11

Ile Leu Ile Asp Trp Leu Val Gln Val
1               5

<210> SEQ ID NO 12
<211> LENGTH: 9
<212> TYPE: PRT
<213> ORGANISM: Homo sapiens

<400> SEQUENCE: 12

Ser Tyr Asn Pro Leu Trp Leu Arg Ile
1               5

<210> SEQ ID NO 13
<211> LENGTH: 9
<212> TYPE: PRT
<213> ORGANISM: Homo sapiens

<400> SEQUENCE: 13

Val Tyr Pro Asn Trp Ala Ile Gly Leu

-continued

<210> SEQ ID NO 14
<211> LENGTH: 9
<212> TYPE: PRT
<213> ORGANISM: Homo sapiens

<400> SEQUENCE: 14

Val Phe Ile Phe Lys Gly Asn Gln Phe
1               5

<210> SEQ ID NO 15
<211> LENGTH: 10
<212> TYPE: PRT
<213> ORGANISM: Homo sapiens

<400> SEQUENCE: 15

Leu Tyr Gln Ile Leu Gln Gly Ile Val Phe
1               5                   10

<210> SEQ ID NO 16
<211> LENGTH: 9
<212> TYPE: PRT
<213> ORGANISM: Homo sapiens

<400> SEQUENCE: 16

Gln Tyr Ala Ser Arg Phe Val Gln Leu
1               5

<210> SEQ ID NO 17
<211> LENGTH: 9
<212> TYPE: PRT
<213> ORGANISM: Homo sapiens

<400> SEQUENCE: 17

Arg Tyr Leu Trp Ala Thr Val Thr Ile
1               5

<210> SEQ ID NO 18
<211> LENGTH: 9
<212> TYPE: PRT
<213> ORGANISM: Homo sapiens

<400> SEQUENCE: 18

Lys Tyr Leu Thr Val Lys Asp Tyr Leu
1               5

<210> SEQ ID NO 19
<211> LENGTH: 10
<212> TYPE: PRT
<213> ORGANISM: Homo sapiens

<400> SEQUENCE: 19

Ile Tyr Asn Gly Lys Leu Phe Asp Leu Leu
1               5                   10

<210> SEQ ID NO 20
<211> LENGTH: 9
<212> TYPE: PRT
<213> ORGANISM: Homo sapiens

<400> SEQUENCE: 20

Ser Tyr Ile Asp Val Leu Pro Glu Phe
1               5

```
<210> SEQ ID NO 21
<211> LENGTH: 9
<212> TYPE: PRT
<213> ORGANISM: Homo sapiens

<400> SEQUENCE: 21

Phe Tyr Ile Ser Pro Val Asn Lys Leu
1               5

<210> SEQ ID NO 22
<211> LENGTH: 9
<212> TYPE: PRT
<213> ORGANISM: Homo sapiens

<400> SEQUENCE: 22

Ala Tyr Leu Val Tyr Thr Asp Arg Leu
1               5

<210> SEQ ID NO 23
<211> LENGTH: 9
<212> TYPE: PRT
<213> ORGANISM: Homo sapiens

<400> SEQUENCE: 23

Asn Tyr Leu Pro Phe Ile Met Glu Leu
1               5

<210> SEQ ID NO 24
<211> LENGTH: 10
<212> TYPE: PRT
<213> ORGANISM: Homo sapiens

<400> SEQUENCE: 24

Tyr Tyr Asn Ala Ala Gly Phe Asn Lys Leu
1               5                   10

<210> SEQ ID NO 25
<211> LENGTH: 9
<212> TYPE: PRT
<213> ORGANISM: Homo sapiens

<400> SEQUENCE: 25

Ala Leu Leu Glu Ser Arg Val Asn Leu
1               5
```

METHOD FOR THE ABSOLUTE QUANTIFICATION OF NATURALLY PROCESSED HLA-RESTRICTED CANCER PEPTIDES

CROSS REFERENCE TO RELATED APPLICATIONS

This application is a continuation of U.S. application Ser. No. 14/969,423 (now U.S. Pat. No. 10,545,154), filed Dec. 15, 2015, which claims priority to U.S. Provisional Application 62/097,994, filed Dec. 30, 2014, and to GB 1423361.3, filed Dec. 30, 2014, the contents of which are incorporated herein by reference in their entireties.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "2912919-040002 Sequence Listing ST25.txt" created on Oct. 23, 2019, and 4,173 bytes in size) is submitted concurrently with the instant application, and the entire contents of the Sequence Listing are incorporated herein by reference.

BACKGROUND

Field of the Invention

The present invention relates to a method for the absolute quantification of naturally processed HLA-restricted cancer peptides, i.e. the determination of the copy number of peptide(s) as presented per cell. The present invention can not only be used for the development of antibody therapies or peptide vaccines, but is also highly valuable for a molecularly defined immuno-monitoring, and useful in the processes of identifying of new peptide antigens for immuno-therapeutic strategies, such as respective vaccines, antibody-based therapies or adoptive T-cell transfer approaches in cancer, infectious and/or autoimmune diseases.

Description of Related Art

Development of cancer immuno-therapeutics and immuno-therapies of autoimmune and infectious diseases aiming to induce the immune system's T-cell arm to fight cancer might be substantially improved by a profound knowledge of human leukocyte antigen (HLA)-bound peptide presentation levels on primary diseased tissues. This information is relevant for antibody-based therapies or peptide vaccines in particular as well as for any other type of T-cell vaccine based on molecular entities such as protein, DNA or RNA. This kind of quantitative data has not been available for patient-derived tissue on an absolute copy per cell-scale before.

A method for identifying peptides as above avoiding the "reverse immunology"-associated problem was disclosed in EP150804761. As described above, this method can not be used for the quantitation of said peptides. Another method employing a labeling strategy was disclosed in WO 2005/076009 which allowed for some quantitation, but not on an absolute scale. Other labels were disclosed, for example, in WO 03/025576 or by Martin et al in Proteomics 2003, 3, 2208-2220.

Another method was disclosed by Fortier et al (The MHC class I peptide repertoire is molded by the transcriptome, JEM, Vol. 205, No. 3, Mar. 17, 2008 595-610). This method has the disadvantages that it requires the dissection of MHC-bound peptides from non-MHC-binding peptides due to acid elution. This is performed using b2m-knockout cell lines: Thus, this method can not be used for primary-patient-tumor materials. In the method, primary murine thymocytes were compared to the murine EL4 cell line. The starting amounts had been adjusted by measuring MHC I molecules. This alone is a strong restriction of the method disclosed by Fortier et al. Furthermore, a normalization as it would be required for primary tissues of different sizes and tissue origin was not applied. Rather, balanced starting materials were used making normalization obsolete. However, normalization is absolutely necessary for primary (patient) materials.

WO2011/128448 discloses a method for quantitatively identifying relevant HLA-bound peptide antigens from primary tissue specimens on a large scale without labeling approaches. The method comprises the steps of providing at least one diseased primary tissue sample and at least one sample of primary healthy tissue preferably corresponding to the diseased tissue, isolating MHC peptide ligands from said sample(s), performing an HPLC-MS analysis on said MHC ligand peptides, extracting the precursor ion signal intensity (area) for each signal, as derived from the analyses, identifying the sequences of said MHC ligand peptides, and normalizing steps and data quality control steps in order to relatively quantify said MHC peptide ligands without labeling.

Hassan et al. (in: Hassan C, et al, Accurate quantitation of MHC-bound peptides by application of isotopically labeled peptide MHC complexes, J Prot (2014), dx.doi.org/10.1016/j.jprot.2014.07.009) disclose an approach in which isotope-labeled peptide-MHC monomers (hpMHC) are prepared and added directly after cell lysis, i.e. before the usual sample processing. Using this approach, all losses during sample processing can be accounted for and allow accurate determination of specific MHC class I-presented ligands. The study pinpoints the immunopurification step as the origin of the rather extreme losses during sample pretreatment and offers a solution to account for these losses. The strategy presented can be used to obtain a reliable view of epitope copy number and thus is said to allow improvement of vaccine design and strategies for immunotherapy.

Stimulation of an immune response is dependent upon the presence of antigens recognized as foreign by the host immune system. The discovery of the existence of tumor associated and disease antigens has raised the possibility of using a host's immune system to intervene in tumor growth. Various mechanisms of harnessing both the humoral and cellular arms of the immune system are currently being explored for cancer immunotherapy.

Specific elements of the cellular immune response are capable of specifically recognizing and destroying tumor cells. The isolation of cytotoxic T-cells (CTL) from tumor-infiltrating cell populations or from peripheral blood suggests that such cells play an important role in natural immune defenses against cancer. CD8-positive T-cells (T-CD8$^+$) in particular, which recognize peptides bound to class I molecules of the major histocompatibility complex (MHC). These peptides of usually 8 to 12 amino acid residues are derived from proteins or defective ribosomal products (DRIPS) located in the cytosol and play an important role in this response. Human MHC-molecules are also designated as human leukocyte-antigens (HLA).

There are two classes of MHC-molecules: MHC class I molecules that can be found on most cells having a nucleus. MHC molecules are composed of an alpha heavy chain and beta-2-microglobulin (MHC class I receptors) or an alpha and a beta chain (MHC class II receptors), respectively. Their three-dimensional conformation results in a binding groove, which is used for non-covalent interaction with peptides. MHC class I present peptides that result from proteolytic cleavage of predominantly endogenous proteins, DRIPs and larger peptides. MHC class II molecules can be found predominantly on professional antigen presenting cells (APCs), and primarily present peptides of exogenous or transmembrane proteins that are taken up by APCs during the course of endocytosis, and are subsequently processed. Complexes of peptide and MHC class I molecules are recognized by CD8-positive cytotoxic T-lymphocytes bearing the appropriate TCR (T-cell receptor), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

For a peptide to trigger (elicit) a cellular immune response, it must bind to an MHC-molecule. This process is dependent on the allele of the MHC-molecule and specific polymorphisms of the amino acid sequence of the peptide. MHC-class-I-binding peptides are usually 8-12 amino acid residues in length and usually contain two conserved residues ("anchors") in their sequence that interact with the corresponding binding groove of the MHC-molecule. In this way, each MHC allele has a binding motif that controls the peptide's ability to specifically bind to the binding groove.

In the MHC class I dependent immune reaction, peptides not only have to be able to bind to certain MHC class I molecules being expressed by tumor cells, they also have to be recognized by T cells bearing specific T cell receptors (TCR).

The antigens that are recognized by the tumor specific cytotoxic T lymphocytes, that is, their epitopes, can be molecules derived from all protein classes, such as enzymes, receptors, transcription factors, etc. which are expressed and, as compared to unaltered cells of the same origin, up-regulated in cells of the respective tumor.

The current classification of tumor associated or disease associated antigens comprises the following major groups:

Cancer-testis antigens: The first TAAs [tumor-associated antigens; disease-associated antigens are abbreviated DAA] ever identified that can be recognized by T cells belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members or NY-ESO-1.

Differentiation antigens: These TAAs are shared between tumors and the normal tissue from which the tumor arose; most are found in melanomas and normal melanocytes. Many of these melanocyte lineage-related proteins are involved in the biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

Over-expressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their over-expression in tumor cells can trigger an anticancer response by breaking previously established tolerance. Prominent examples for this class of TAAs are Her-2/neu, Survivin, Telomerase or WT1.

Tumor specific antigens: These unique TAAs arise from mutations of normal genes (such as β-catenin, CDK4, etc.). Some of these molecular changes are associated with neoplastic transformation and/or progression. Tumor specific antigens are generally able to induce strong immune responses without bearing the risk for autoimmune reactions against normal tissues. On the other hand, these TAAs are in most cases only relevant to the exact tumor on which they were identified and are usually not shared between many individual tumors. TAAs arising from abnormal post-translational modifications: Such TAAs may arise from proteins which are neither specific nor over-expressed in tumors but nevertheless become tumor associated by posttranslational processes primarily active in tumors. Examples for this class arise from altered glycosylation patterns leading to novel epitopes in tumors as for MUC1 or events like protein splicing during degradation which may or may not be tumor specific.

Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

For proteins to be recognized by cytotoxic T-lymphocytes as tumor-specific or -associated antigens or disease-specific or -associated antigens, and to be used in a therapy, particular prerequisites must be fulfilled. The antigen should be expressed mainly by tumor cells or infected cells and not at all or only in comparably small amounts by normal healthy tissues, for example less by the factor 5, 10 or more.

In infectious diseases there are two possibilities, first the infected cells express an antigen not expressed by healthy cells—directly associated to the infection—or the infected cells over-express an antigen expressed only in very small amounts by healthy cells—the over-expression of an antigen normally found in the peptidome of a healthy cell.

It is furthermore desirable, that the respective antigen is not only present in a type of tumor, infection or strain, but also in high concentrations (i.e. copy numbers of the respective peptide per cell). Tumor-specific and tumor-associated antigens and disease-specific or disease-associated antigens are often derived from proteins directly involved in transformation of a normal cell to a tumor/infected cell due to a function e.g. in cell cycle control or suppression of apoptosis.

In the case of cancer, additional downstream targets of the proteins directly causative for a transformation may be upregulated and thus may be indirectly tumor-associated. Such indirect tumor-associated antigens may also be targets of a vaccination approach (Singh-Jasuja H., Emmerich N. P., Rammensee H. G., Cancer Immunol. Immunother. 2004 March; 453 (3): 187-95). In both cases, it is essential that epitopes are present in the amino acid sequence of the antigen, since such a peptide ("immunogenic peptide") that is derived from a tumor associated or disease associated antigen should lead to an in vitro or in vivo T-cell-response.

Basically, any peptide which is able to bind a MHC molecule may function as a T-cell epitope. A prerequisite for the induction of an in vitro or in vivo T-cell-response is the presence of a T cell with a corresponding TCR and the absence of immunological tolerance for this particular epitope.

Therefore, TAAs and DAAs are a starting point for the development of a tumor vaccine. The methods for identifying and characterizing the TAAs and DAAs are based on the use of CTL that can be isolated from patients or healthy subjects, or they are based on the generation of differential transcription profiles or differential peptide expression patterns between tumors and normal tissues.

However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and immunological tolerance for this particular epitope needs to be absent or minimal. It is therefore important to select only those peptides from over-expressed or selectively expressed proteins that are presented in connection with MHC molecules against which a functional T cell can be found. Such a functional T cell is defined as a T cell which upon stimulation with a specific antigen can be clonally expanded and is able to execute effector functions ("effector T cell").

T-helper cells play an important role in orchestrating the effector function of CTLs in anti-tumor immunity. T-helper cell epitopes that trigger a T-helper cell response of the TH1 type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions which stimulate anti-tumor immune responses.

Knowledge of the accurate copy number of HLA class I or II presented ligands is important in fundamental and clinical immunology. Currently, the best copy number determinations are based on mass spectrometry, employing single reaction monitoring (SRM) in combination with a known amount of isotopically labeled peptide. Nevertheless, these approaches are still not precise enough in order to be efficiently employed in the above approaches.

SUMMARY

In view of the above, it is therefore the object of the present invention to provide a method for an absolute determination of copy numbers of HLA class I or II presented ligands which is precise, efficient, easy to handle, and also can be performed on a "high-throughput" level. Other objects and advantages of the present invention will become readily apparent for the person of skill when studying the following description as provided.

In a first aspect of the present invention, the object of the invention is solved by a method for the absolute quantification of at least one MHC peptide ligand on a cell, said method comprising
a) preparing cells presenting said at least one MHC peptide ligand from a biological sample comprising cells,
b) determining the cell count of said preparation of step a),
c) adding a known amount of said at least one peptide-MHC ligand and/or peptide-MHC ligandcomplex to be quantified to said preparation of step a) ("spiking I"),
d) isolating at least one MHC peptide ligand from said preparation of step c) in order to obtain a peptide eluate,
e) adding a known amount of at least one MHC peptide ligand to be quantified to said peptide eluate ("spiking II"),
f) performing a mass spectrometry analysis on said at least one MHC peptide ligand in order to generate at least one
    aa) signal for the efficiency of the isolation in step d),
    bb) signal for the known amount of said at least one MHC peptide ligand as added in step e), and
    cc) signal for said at least one MHC peptide ligand from said prepared cells of step a), and;
g) quantifying said at least one MHC peptide ligand based on a comparison of the signals as obtained in step f) with
    aa) the cell count as obtained,
    bb) the known amount of said at least one peptide-MHC ligand and/or peptide-MHC ligand complex to be quantified as added in step c), and
    cc) the known amount of at least one MHC peptide ligand to be quantified as added in step e),
whereby an absolute quantification of at least one MHC peptide ligand on a cell is, at least in part, achieved.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF A PREFERRED EMBODIMENT

Figure 1:
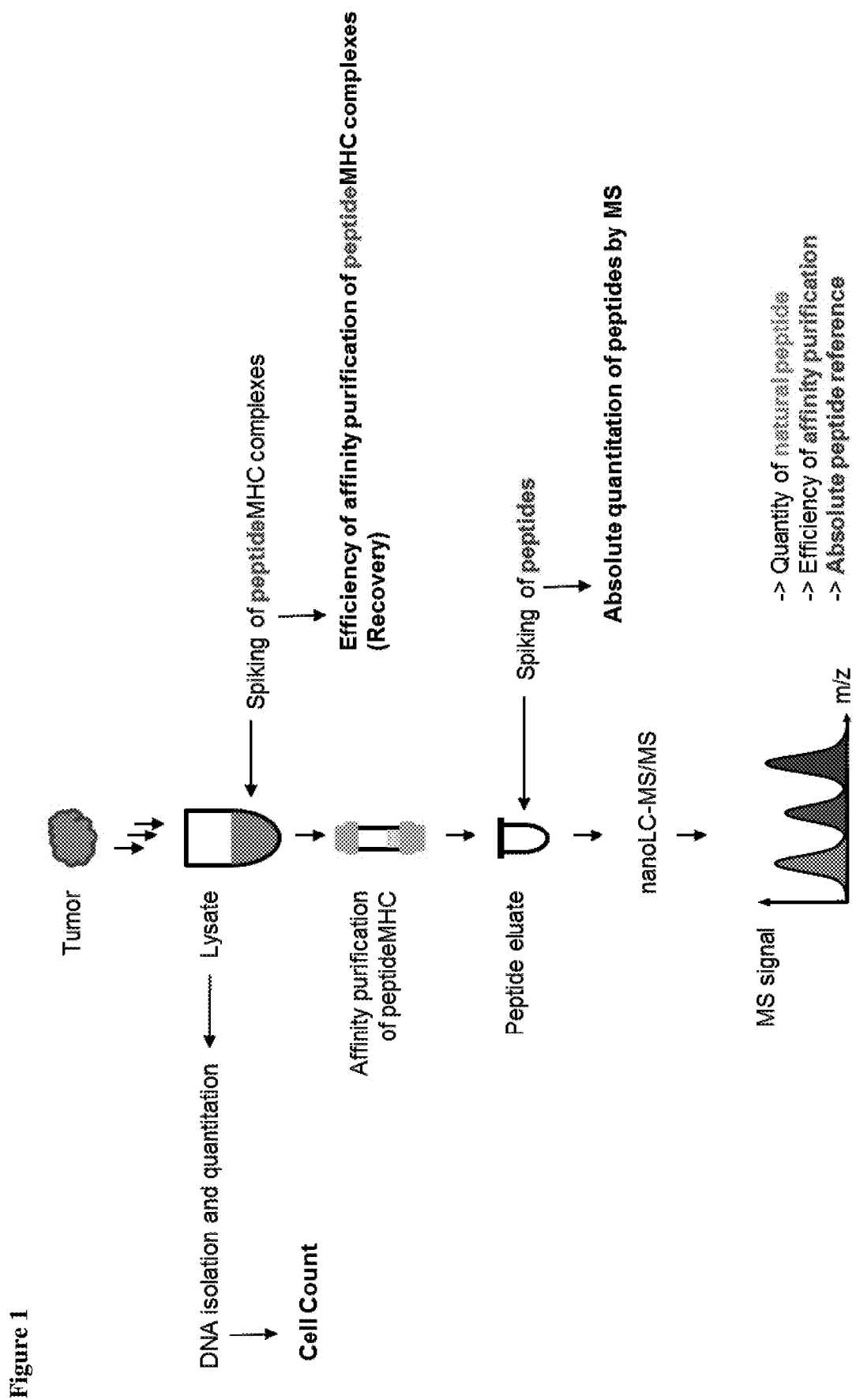
FIGS. 1-17 depict embodiments as described herein.

In a method according to the present invention, where several samples are analyzed in parallel, step c) as above can be omitted once the isolation efficiency has been established, as the efficiency for one sample can be used to estimate the isolation efficiency for a second MHC peptide ligand and/or MHC peptide ligand complex (i.e. can be used as a cross-reference value).

Preferred is a method which furthermore uses the signal obtained from the internal calibration (spiking II) in e) as a constant and preserved (control) reference for the signal obtained from the isolated at least one MHC peptide ligand by calculating a ratio between these two signals. This ratio is compared with the established calibration curve, which also includes the internal calibrant at the very same amount, preferably by using an identical aliquot of such internal calibrant. The calibration curve then describes the relation between these ratios and the amounts of peptide. See also FIG. 3 and the legend thereof.

Surprisingly, in the context of the present invention the inventors found that by combining the above analysis steps, for the first time, direct absolute quantitation of MHC-, preferably HLA-restricted, peptide levels on cancer or other infected tissues in comparison to several different non-cancerous tissues or no-infected tissues and organs becomes possible.

In the context of the present invention, "spiking" refers to the addition of a known amount or concentration of at least one known, for example unbound ("free") MHC peptide ligand to be quantified to a sample, such as, for example, a preparation (here designated as "spiking I") or a peptide eluate (here designated as "spiking II"). The amounts/concentrations of peptide(s) to be added can be readily adjusted and depend at least in part on the sample to be spiked and the method used for the analysis.

Preferred is a method according to the present invention, wherein at least one MHC peptide ligand is selected from a tumor associated peptide (TAA) or disease associated peptide (DAA).

Further preferred is a method according to the present invention wherein said biological sample comprising cells is selected from a tissue sample, a blood sample, a tumor sample, or a sample of an infected tissue. In the context of the present invention, samples that are directly derived from subjects, such as patients, are termed "primary" samples, such as primary tissue or tumor samples, in contrast to samples of cell lines, such as, for example, established tumor cell lines. The samples can be fresh or conserved (e.g. frozen or prepared), as long as they are suitable for the method according to the invention. Preferred is a biological sample that does not include permanent cell lines.

As a preferred example, the HLA peptide pools from shock-frozen (primary) tissue samples can be obtained by immune precipitation from solid tissues using for example the HLA-A, -B, -C-specific antibody w6132 or the HLA-A*02-specific antibody BB7.2 coupled to CNBr-activated sepharose, followed by acid treatment, and ultrafiltration. For different HLA-alleles other specific antibodies known in the art can be used as there are for example GAP-A3 for A*03, B1.23.2 for B-alleles. There are corresponding methods to obtain MHC-class I peptides for other mammals that are well known in the art.

The method according to the invention can also be used in the context of infectious diseases, such as viral or bacterial infections, for example dengue fever, Ebola, Marburg virus, tuberculosis (TB), meningitis or syphilis, preferable the method is used on antibiotic-resistant strains of infectious organisms, autoimmune diseases, such as arthritis, parasitic infections, such as malaria and other diseases such as MS and Morbus Parkinson, as long as the targeted moiety is a MHC class I-bound peptide.

Examples for autoimmune diseases (including diseases not officially declared to be autoimmune diseases) are Chronic obstructive pulmonary disease, Ankylosing Spondylitis, Crohn's Disease (one of two types of idiopathic inflammatory bowel disease "IBD"), Dermatomyositis, Diabetes mellitus type 1, Endometriosis, Goodpasture's syndrome, Graves' disease, Guillain-Barre syndrome (GBS), Hashimoto's disease, Hidradenitis suppurativa, Kawasaki disease, IgA nephropathy, Idiopathic thrombocytopenic purpura, Interstitial cystitis, Lupus erythematosus, Mixed Connective Tissue Disease, Morphea, Myasthenia gravis, Narcolepsy, Neuromyotonia, Pemphigus vulgaris, Pernicious anemia, Psoriasis, Psoriatic Arthritis, Polymyositis, Primary biliary cirrhosis, Relapsing polychondritis, Rheumatoid arthritis, Schizophrenia, Scleroderma, Sjogren's syndrome, Stiff person syndrome, Temporal arteritis (giant cell arteritis), Ulcerative Colitis (one of two types of idiopathic inflammatory bowel disease "IBD"), Vasculitis, Vitiligo and Wegener's granulomatosis.

The present invention is not restricted to human diseases, but can be used for mammals, for example cows, pigs, horses, cats, dogs, rodents, such as rat, mouse, goat, and other domestic animals.

In yet another preferred embodiment of the method according to the present invention, preparing of cells comprises, at least in part, enzymatic digestion of tissues, and/or cellular lysis.

Preferred is a method according to the present invention, wherein said cell count is determined using a method selected from counting cell nuclei, photometric DNA-determination, fluorimetric DNA-determination (such as, for example, using the Qubit® technology), and quantitative PCR.

Further preferred is a method according to the present invention, further comprising determining the amount of at least one type of HLA-molecule in said preparation of step a). Determining the amount can be done using common methods in the art, such as methods involving specific antibodies e.g. in an ELISA, gels, cell sorting, and/or chromatography.

Further preferred is a method according to the present invention, wherein the at least one peptide-MHC complex as added and/or the least one MHC peptide ligand as added are labeled, and preferably are differentially labeled. Respective labels are known to the person of skill, and include isotopic labels, radioactive and non-radioactive labels, enzymes, and other groups of preferably different masses. Preferably, the labeling is specific for specific peptides to be quantified. Most preferred is a double-labeled TAA/TUMAP, for example in situations in which two differentially labeled spikings are required in the same experiment (see examples, below).

Preferred is a method according to the present invention, wherein isolating comprises chromatography, such as affinity chromatography. Thus, the isolated MHC/HLA ligands can be separated according to their hydrophobicity by reversed-phase chromatography (e.g. nanoAcquity UPLC system, Waters) followed by detection in an Orbitrap hybrid mass spectrometer (ThermoElectron). Each sample is preferably analyzed by acquisition of replicate (e.g.) LCMS runs. The LCMS data is then processed by analyzing the Tandem-MS (MS/MS) data.

The tandem-MS spectra recorded in a targeted way focusing on the m/z values of the peptides to be quantified are evaluated preferably by a software that extracts the intensities of pre-selected fragment ions of pre-defined transitions. One example of such a software is Skyline (MacLean B et al. Skyline: an open source document editor for creating and analyzing targeted proteomics experiments. Bioinformatics. 2010 Apr. 1; 26(7):966-8., dx.doi.org/10.1093/bioinformatics/btq054), an application for analyzing mass spectrometer data of data independent acquisition (DIA) experiments for parallel reaction monitoring (PRM—targeted MS/MS). This software can be used with respect to the co-eluting isotope-labeled peptide for specificity purposes as well as in order to extract the single transition intensities for further processing.

Comparability of peptide groups restricted to the same HLA allele between different samples is possible based on a common allele-specific antibody used for purification, if available, or alternatively based on assignment of sequences to common HLA-alleles by means of anchor amino acid patterns.

For statistic reasons, preferred is a method according to the present invention, wherein at least two replicate mass spectrometry runs are performed for each at least one MHC ligand peptide.

Thus, yet another aspect of the present invention relates to a method according to the present invention, further comprising selecting overrepresented, overexpressed and/or tumor-specific MHC peptide ligands for the analysis.

Yet another aspect of the present invention relates to a method according to the present invention, wherein said method is capable of being performed or is performed on a high-throughput basis, preferably up to 50 to 100 peptide ligands can be analyzed in parallel.

In still another preferred embodiment of the method according to the present invention, the steps of said method are performed in the order as indicated in the appended claims, or as above. In still another preferred method according to the present invention said method consists of the steps as indicated above and herein.

In a further preferred aspect of the method according to the present invention, said method relates to personalized therapy and diagnosis. For this, said sample(s) as analyzed is/are derived from one individual, or from a group of individuals suffering from the same medical condition as described herein. Also, a personalized MHC ligand profile, preferably a personalized quantified disease-specific MHC ligand profile, based on said MHC peptide ligands as quantified can be generated based on the method according to the present invention as described herein.

Most preferably, the method according to the present invention is performed in vitro.

In a further preferred aspect of the method according to the present invention, said method further comprises the step of synthesizing, preferably chemically synthesizing, said at least one MHC peptide ligand as quantified by said method on a synthesizer or manually. Another aspect of the invention thus relates to a method for preparing an immunoreactive peptide with which a peptide is quantified according to the disclosed method and said peptide is synthesized chemically, in vitro or in vivo. Peptides can be prepared by chemical linkage of amino acids by the standard methods known in the art.

Peptides can be prepared in vitro, for example, in cell-free systems, and in vivo using cells. The peptides can be formulated as disclosed, for example, in EP2111867 by Lewandrowski et al.

Yet another aspect relates to the method according to the invention, wherein a further step is performed, in which the presence of the T-lymphocytes is detected. Using this method, it is possible to specifically detect to what extent T-lymphocytes directed against isolated and identified peptides are pre-existing in patients. By performing this step it is possible to apply, as a vaccine, only those peptides against which T-lymphocytes are already pre-existing in the patient. The peptides can then be used to activate these specific T-lymphocytes.

A further aspect relates to the method according to the invention, wherein the detection of specific pre-existing T-lymphocytes is performed by labeling the leukocytes with reconstituted complexes of antigen-presenting molecules and antigenic peptide.

In yet another preferred embodiment of the method according to the present invention, said method does furthermore exclude the use of knock-out cells, cell lines or animals.

A further preferred optional step of the present invention is an automatic quality control based on molecules spiked into the samples in defined amounts.

With the method according to the invention it is furthermore possible to identify patient-specific peptides, i.e. it is possible to precisely match peptides, which are to be used as vaccine, to the patient in order to induce a specific immune response.

Another aspect of the invention then relates to a pharmaceutical composition comprising defined amounts of one or more TAA and/or DAA peptides that have been quantified by the method according to the invention.

The composition may be applied, for example, parenterally, for example subcutaneously, intradermally or intramuscularly, or may be administered orally, depending on the formulation and the target disease. In doing so, the peptides are dissolved or suspended in a pharmaceutically acceptable carrier, preferably an aqueous carrier; the composition can further comprise additives, for example buffers, binders, etc. The peptides can also be administered together with immunostimulating substances, for example cytokines.

According to one aspect of the invention, the peptides may be used for the treatment of tumorous diseases and for preparing a drug for treatment of tumor diseases. Tumorous diseases to be treated comprise solid tumors, such as renal, breast, pancreas, gastric, testis and/or skin cancer or blood cancers, such as AML. This list of tumor diseases is only exemplary, and is not intended to limit the area of application.

The peptides can further be used for assessment of the therapy-course of a tumor disease.

The peptides can also be used for monitoring a therapy in other immunizations or therapies. Therefore, the peptide may not only be used therapeutically but also diagnostically.

A further aspect of the invention then relates to the use of the peptides as quantified for generating an antibody. Polyclonal antibodies can be obtained, in a general manner, by immunization of animals by means of injection of the peptides and subsequent purification of the immunoglobulin. Monoclonal antibodies can be generated according to standardized protocols known in the art.

The present invention is of particular relevance for antibody-based approaches, as the target's copy number on the cell surface of a target cell determines and/or reflects, if the target is addressable for an antibody at all, and, if so, which effector functions can be used, such as conjugated drugs, toxins, bispecific antibodies recruiting T cells or other effector cells. Other aspects relates to the use in the context of so-called scaffolding forming molecules, such as aptamers (target-binding oligonucleic acid or peptide molecules) and/or soluble T cell receptors (TCRs). Here again, similar as for antibodies, the copy number determines about required avidities and effector functions. For said scaffolding molecules.

Stimulation of an immune response is dependent upon the presence of antigens recognized as foreign by the host immune system. The discovery of the existence of tumor associated antigens has now raised the possibility of using a host's immune system to intervene in tumor growth. Various mechanisms of harnessing both the humoral and cellular arms of the immune system are currently explored for cancer immunotherapy.

Specific elements of the cellular immune response are capable of specifically recognizing and destroying tumor cells. The isolation of cytotoxic T-cells (CTL) from tumor-infiltrating cell populations or from peripheral blood suggests that such cells play an important role in natural immune defenses against cancer. CD8-positive T-cells in particular, which recognize class I molecules of the major histocompatibility complex (MHC)-bearing peptides of usually 8 to 12 residues derived from proteins or defect ribosomal products (DRIPS) located in the cytosols, play an important role in this response. The MHC-molecules of the human are also designated as human leukocyte-antigens (HLA).

MHC class I molecules can be found on most cells having a nucleus which present peptides that result from proteolytic cleavage of mainly endogenous, cytosolic or nuclear proteins, DRIPS, and larger peptides. However, peptides derived from endosomal compartments or exogenous sources are also frequently found on MHC class I molecules. This non-classical way of class I presentation is referred to as cross-presentation in literature.

For proteins to be recognized by cytotoxic T-lymphocytes as tumor-specific or -associated antigens, and to be used in a therapy, particular prerequisites must be fulfilled. The antigen should be expressed mainly by tumor cells and not by normal healthy tissues or in comparably small amounts. It is furthermore desirable, that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to a function e.g. in cell cycle control or apoptosis. Additionally, also downstream targets of the proteins directly causative for a transformation may be upregulated and thus are indirectly tumor-associated. Such indirect tumor-associated antigens may also be targets of a vaccination approach. Essential is in both cases the presence of epitopes in the amino acid sequence of the antigen, since such peptide ("immunogenic peptide") that is derived from a tumor associated or disease associated antigen should lead to an in vitro or in vivo T-cell-response.

Basically, any peptide able to bind a MHC molecule may function as a T-cell epitope. A prerequisite for the induction of an in vitro or in vivo T-cell-response is the presence of a T cell with a corresponding TCR and the absence of immunological tolerance for this particular epitope. Therefore, TAAs are a starting point for the development of a tumor vaccine. The methods for identifying and characterizing the TAAs are based on the use of CTL that can be isolated from patients or healthy subjects, or they are based on the generation of differential transcription profiles or differential peptide expression patterns between tumors and normal tissues (Lemmel et al. 450-54; Weinschenk et al. 5818-27). However, the identification of genes over-expressed in tumor tissues or human tumor cell lines, or selectively expressed in such tissues or cell lines, does not provide precise information as to the use of the antigens being transcribed from these genes in an immune therapy. This is because only an individual subpopulation of epitopes of these antigens are suitable for such an application since a T cell with a corresponding TCR has to be present and immunological tolerance for this particular epitope needs to be absent or minimal. It is therefore important to select only those peptides from over-expressed or selectively expressed proteins that are presented in connection with MHC molecules against which a functional T cell can be found. Such a functional T cell is defined as a T cell that upon stimulation with a specific antigen can be clonally expanded and is able to execute effector functions ("effector T cell").

Considering the severe side-effects and expenses associated with treating cancer, better prognostic and diagnostic methods are desperately needed.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, 12, 13 or 14 amino acids in length.

The term "oligopeptide" is used herein to designate a series of amino acid residues, connected one to the other typically by peptide bonds between the alpha-amino and carbonyl groups of the adjacent amino acids. The length of the oligopeptide is not critical to the invention, as long as the correct epitope or epitopes are maintained therein. The oligopeptides are typically less than about 30 amino acid residues in length, and greater than about 14 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus an "immunogen" within the present invention), if it is capable of inducing an immune response. In the case of the present invention, immunogenicity is more specifically defined as the ability to induce a T-cell response. Thus, an "immunogen" would be a molecule that is capable of inducing an immune response, and in the case of the present invention, a molecule capable of inducing a T-cell response.

A T cell "epitope" requires a short peptide that is bound to a class I MHC receptor, forming a ternary complex (MHC class I alpha chain, beta-2-microglobulin, and peptide) that can be recognized by a T cell bearing a matching T-cell receptor binding to the MHC/peptide complex with appropriate affinity. Peptides binding to MHC class I molecules are typically 8-14 amino acids in length, and most typically 9 amino acids in length.

In the present description, the invention is described using cancer as an example. Nevertheless, the inventive method can also be applied in infectious diseases, autoimmune diseases, and parasitic infections as long as the respective immune answer is a MHC class I involving answer.

The invention shall now be described further in the following examples, nevertheless, without being limited thereto. In the accompanying Figures and the Sequence Listing, FIG. 1: shows a general schematic overview over the experimental approach according to the present invention.

Figure 2:
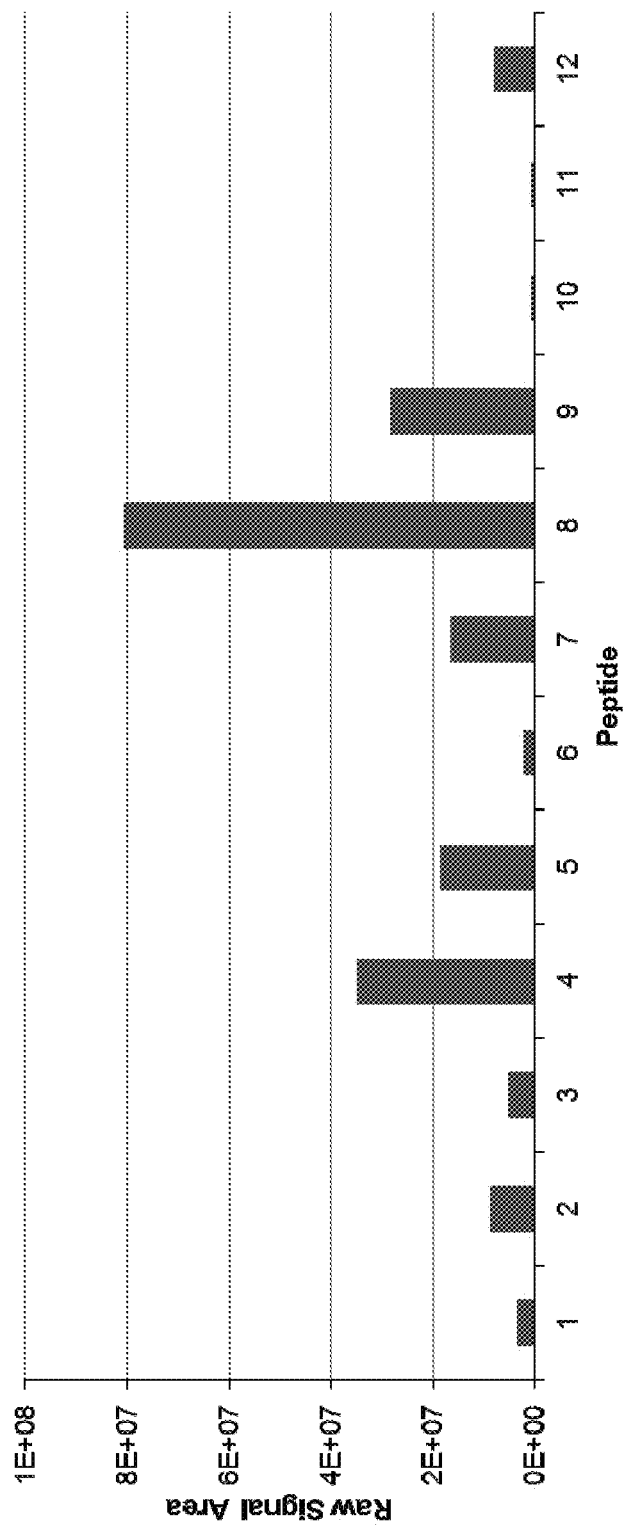

FIG. 2: shows a comparative MS analysis of a TUMAP mix with 10 fmol per TUMAP of table 1. Each peptide results in a different MS signal showing the peptide-dependent detectability. Peptide 5 is not listed in table 1, i.e. the sequences 1~4 in table 1 correspond to Nos. 1 to 4 in FIG. 2 and sequences 5-11 in table 1 correspond to Nos. 6 to 12 in FIG. 2.

Furthermore, Peptides 19, 21, and 22 in FIG. 2 are not listed in table 2, i.e. the sequences 13-18 in FIG. 2 correspond to Nos. 12 to 17 in table 2, sequence 20 in FIG. 2 corresponds to No 18 in Table 2, and sequences 23 to 28 in FIG. 2 corresponds to Nos 19-24 in Table 2.

Figure 3:
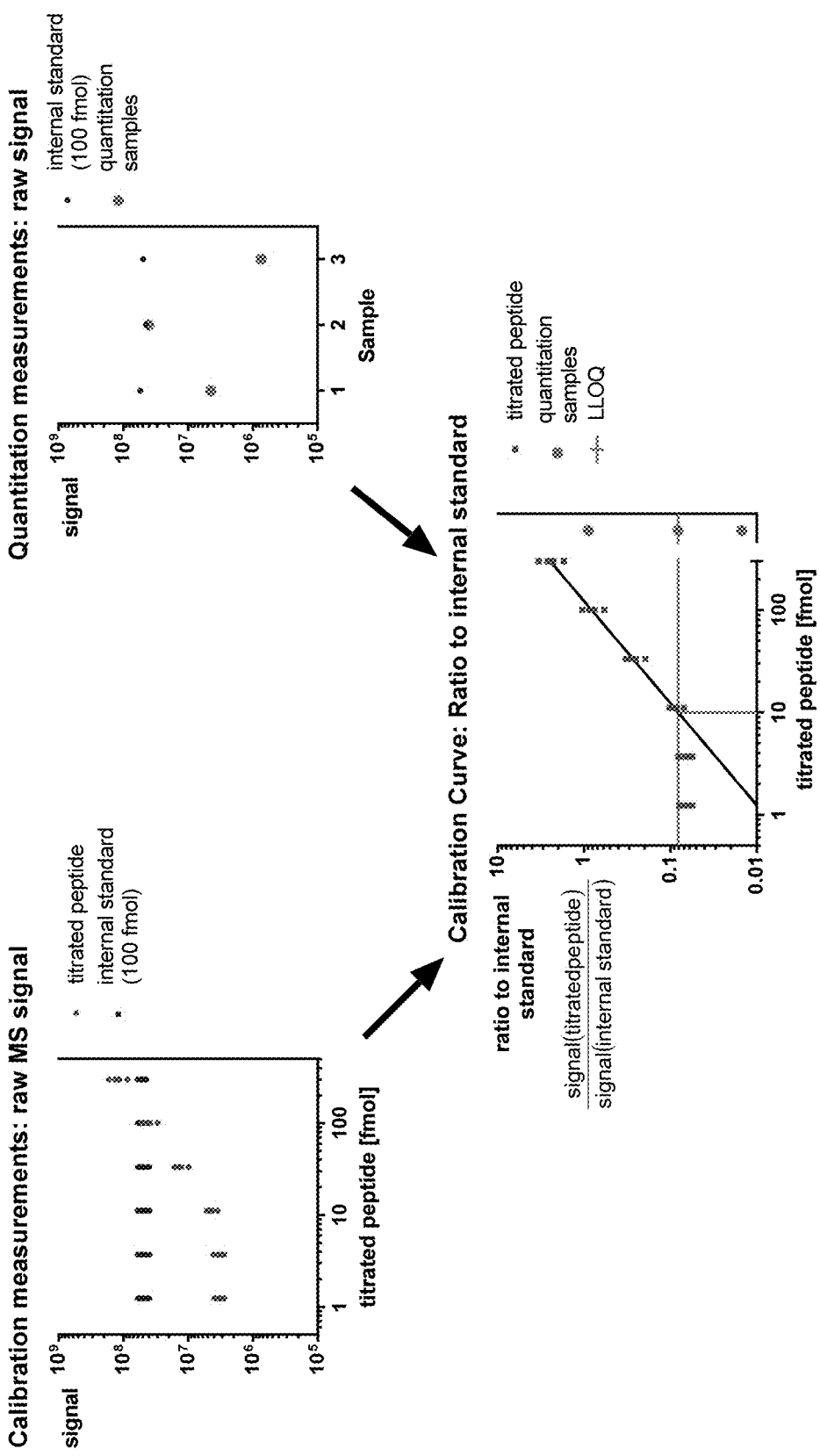

FIG. 3: shows the principle of the internal standard method. A calibration curve is generated by titration of an isotope-labeled version (depicted in light gray) of the TUMAP. For all MS measurements, a constant quantity of another isotope-labeled version of the TUMAP internal standard peptide (depicted in dark gray) is spiked into the MS samples. A calibration curve function is calculated from the ratio of MS signals by logistic regression. The LLOQ is defined by visual examination and considering the deviation from linearity. "Quantitation samples" (depicted in green) represent signal intensities measured in tumor samples selected for absolute quantitation of TUMAP numbers.

Figure 4:
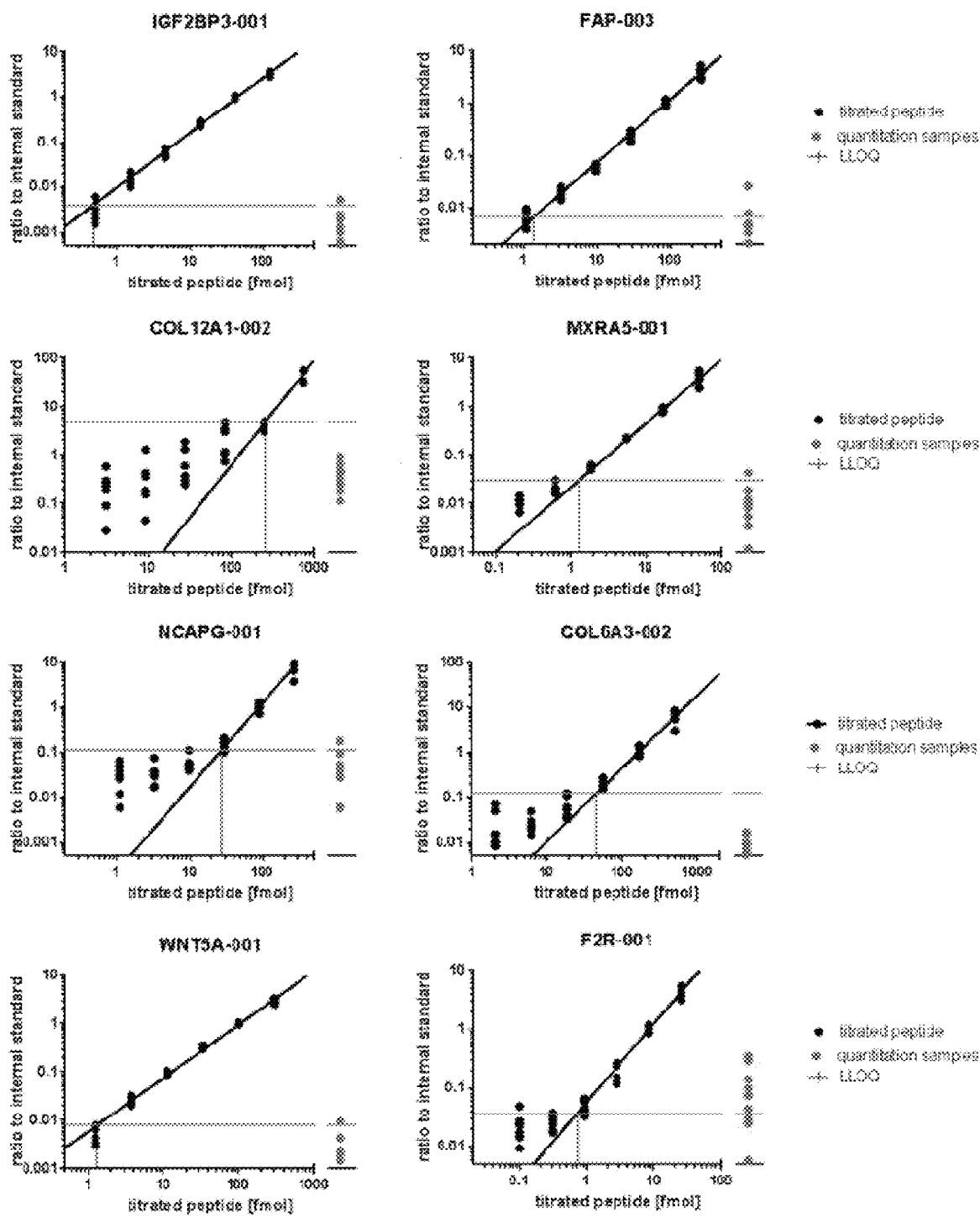

FIG. 4: shows calibration curves of the HLA-A*02 TUMAPs selected for absolute quantitation. The MS results of the respective TUMAPs in tumor tissue samples used for analysis of absolute TUMAP numbers per cell ("quantitation samples") are included in each chart.

Figure 5:
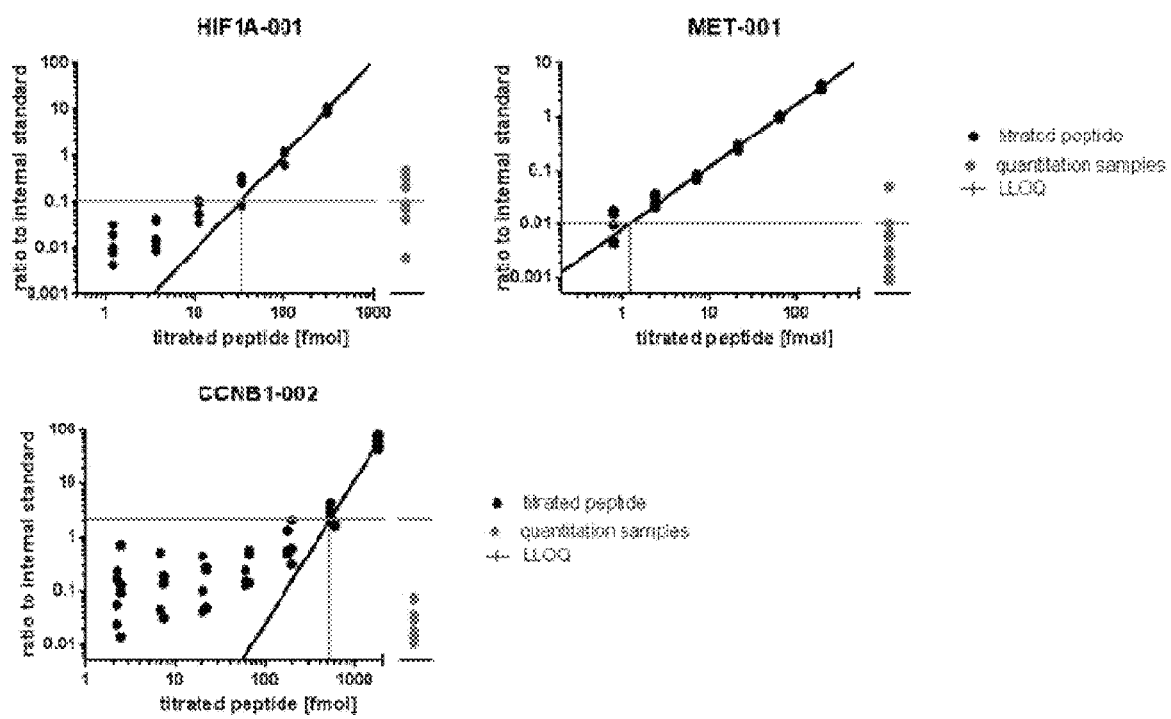

FIG. 5: shows additional calibration curves of the HLA-A*02 TUMAPs selected for absolute quantitation. The MS results of the respective TUMAPs in tumor tissue samples used for analysis of absolute TUMAP numbers per cell ("quantitation samples") are included in each chart.

Figure 6:
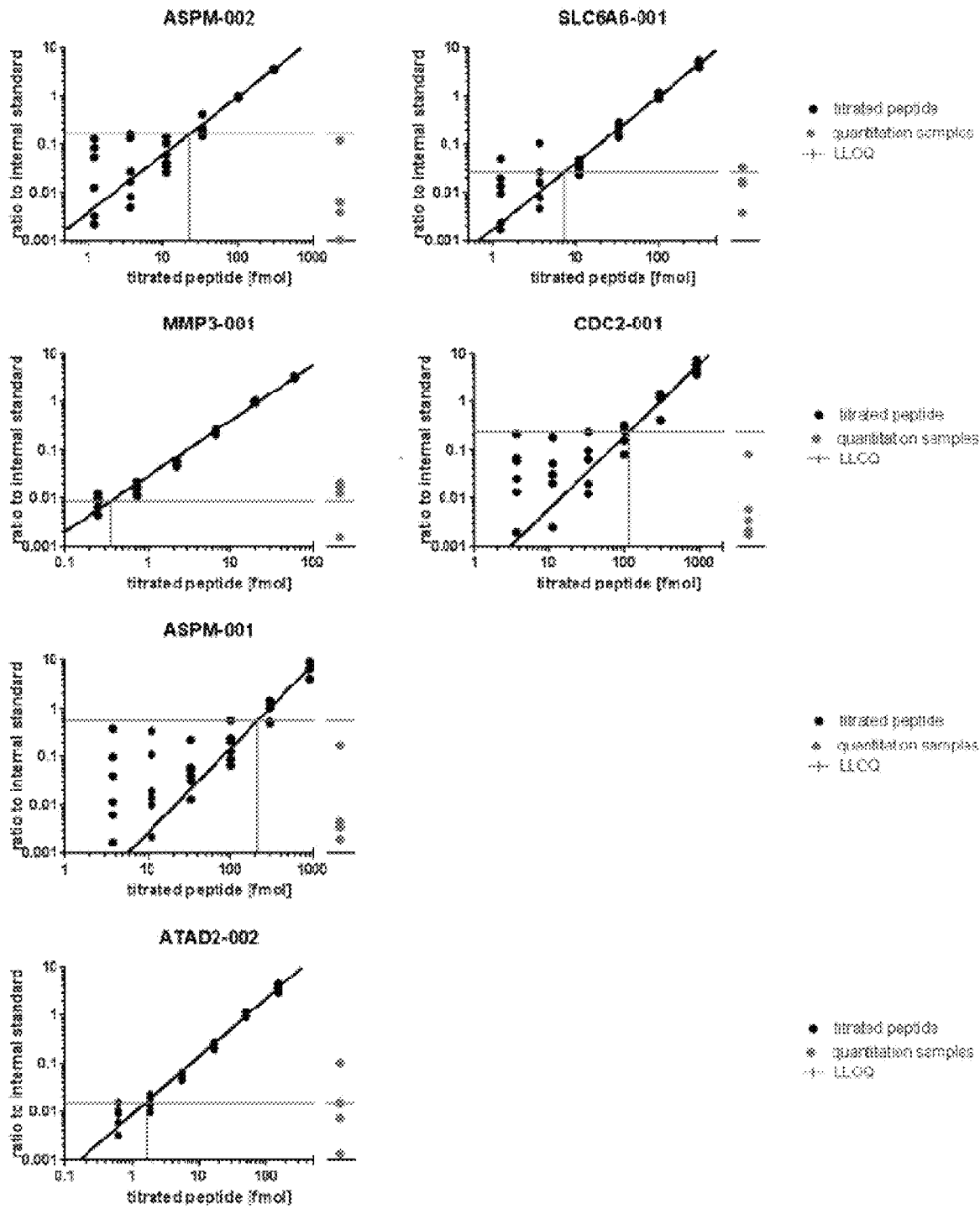
Figure 7:
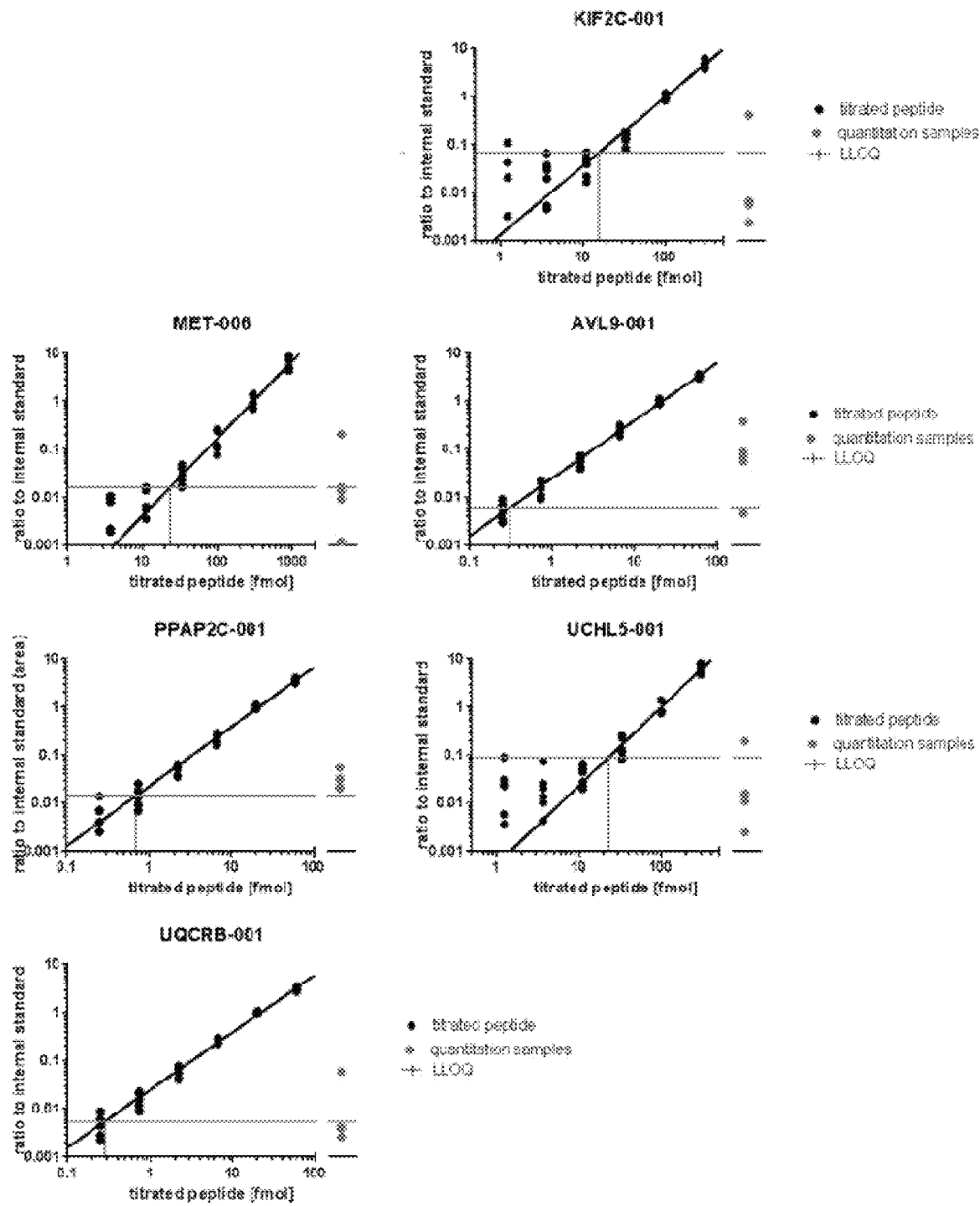

FIG. 6: shows calibration curves of the HLA-A*24 TUMAPs selected for absolute quantitation. The MS results of the respective TUMAPs in tumor tissue samples used for analysis of absolute TUMAP numbers per cell ("quantitation samples") are included in each chart FIG. 7: shows additional calibration curves of the HLA-A*24 TUMAPs selected for absolute quantitation. The MS results of the respective TUMAPs in tumor tissue samples used for analysis of absolute TUMAP numbers per cell ("quantitation samples") are included in each chart.

Figure 8:
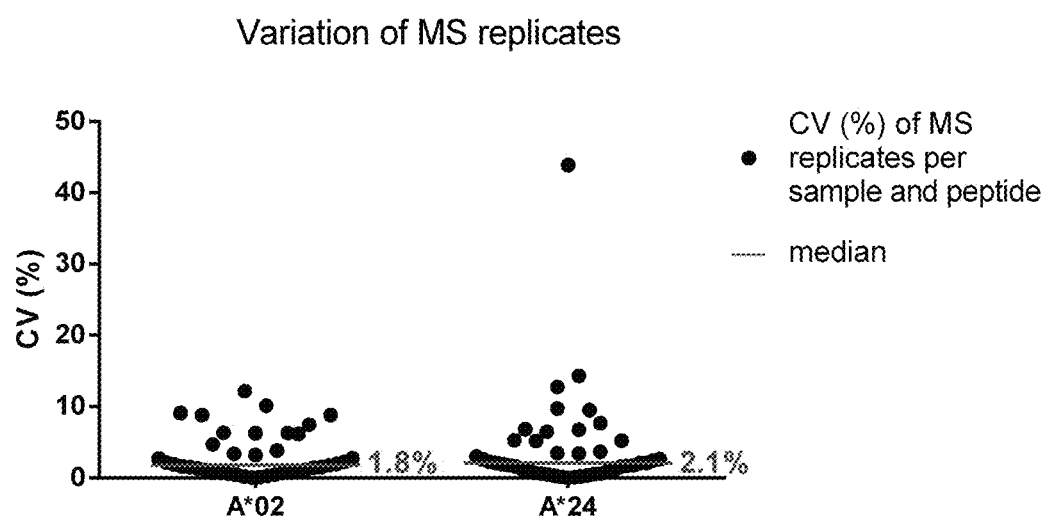

FIG. 8: shows the estimated variation of MS replicate measurements over all TUMAPs analyzed. Each dot represents the coefficient of variation (CV in %) for MS replicates of an individual TUMAP in one specific tissue sample. The median of the CVs over all TUMAPs is regarded as average variation of MS replicate runs.

Figure 9:
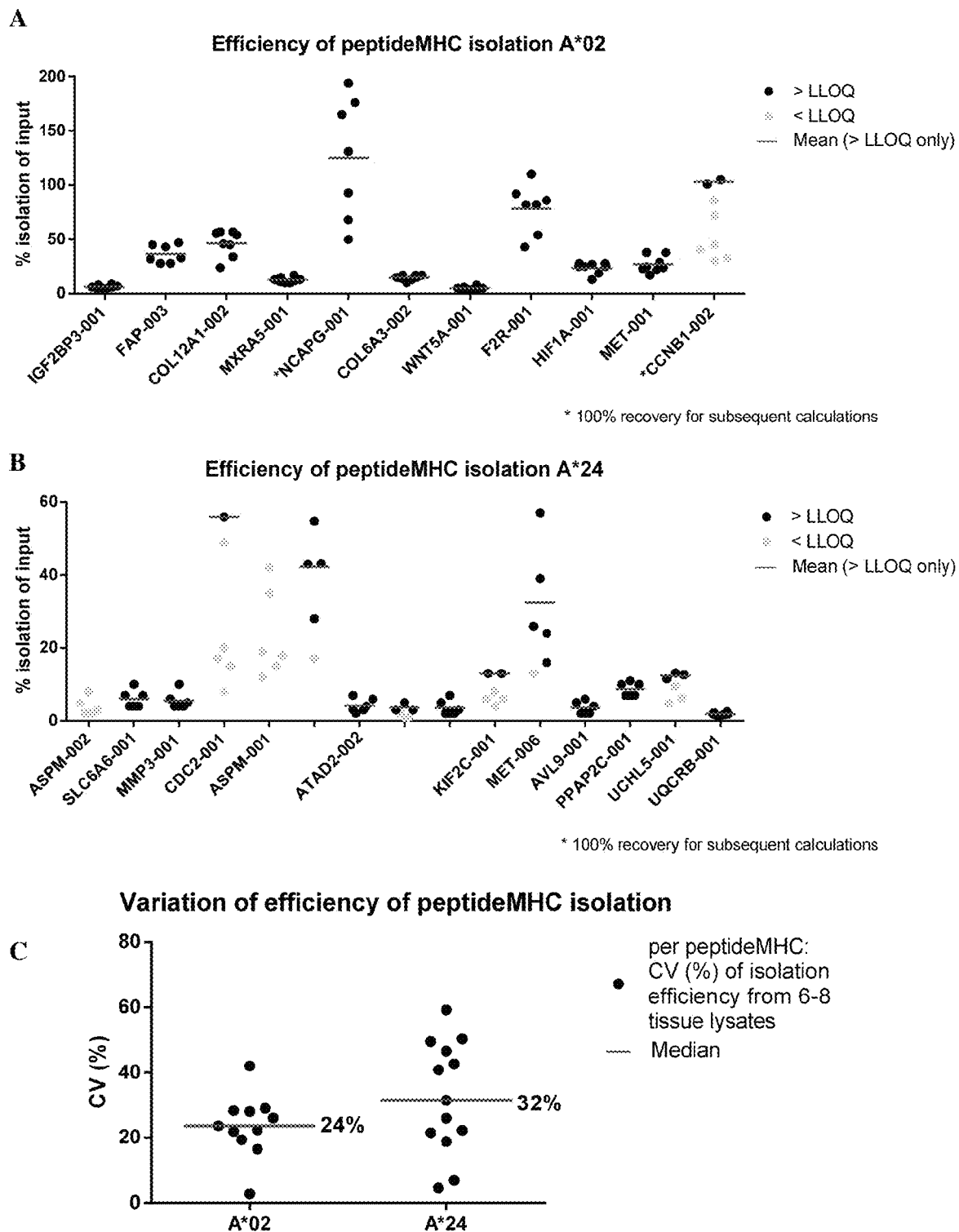

FIG. 9: shows the efficiency of the peptideMHC isolation. The efficiency of peptideMHC isolation was determined in eight A*02-positive samples for A*02 TUMAPs (A), and in six A*24-positive samples for A*24 TUMAPs (B). The efficiency of isolation varies on average 24% for A*02 TUMAPs and 32% for A*24 TUMAPs, respectively (C).

Figure 10:
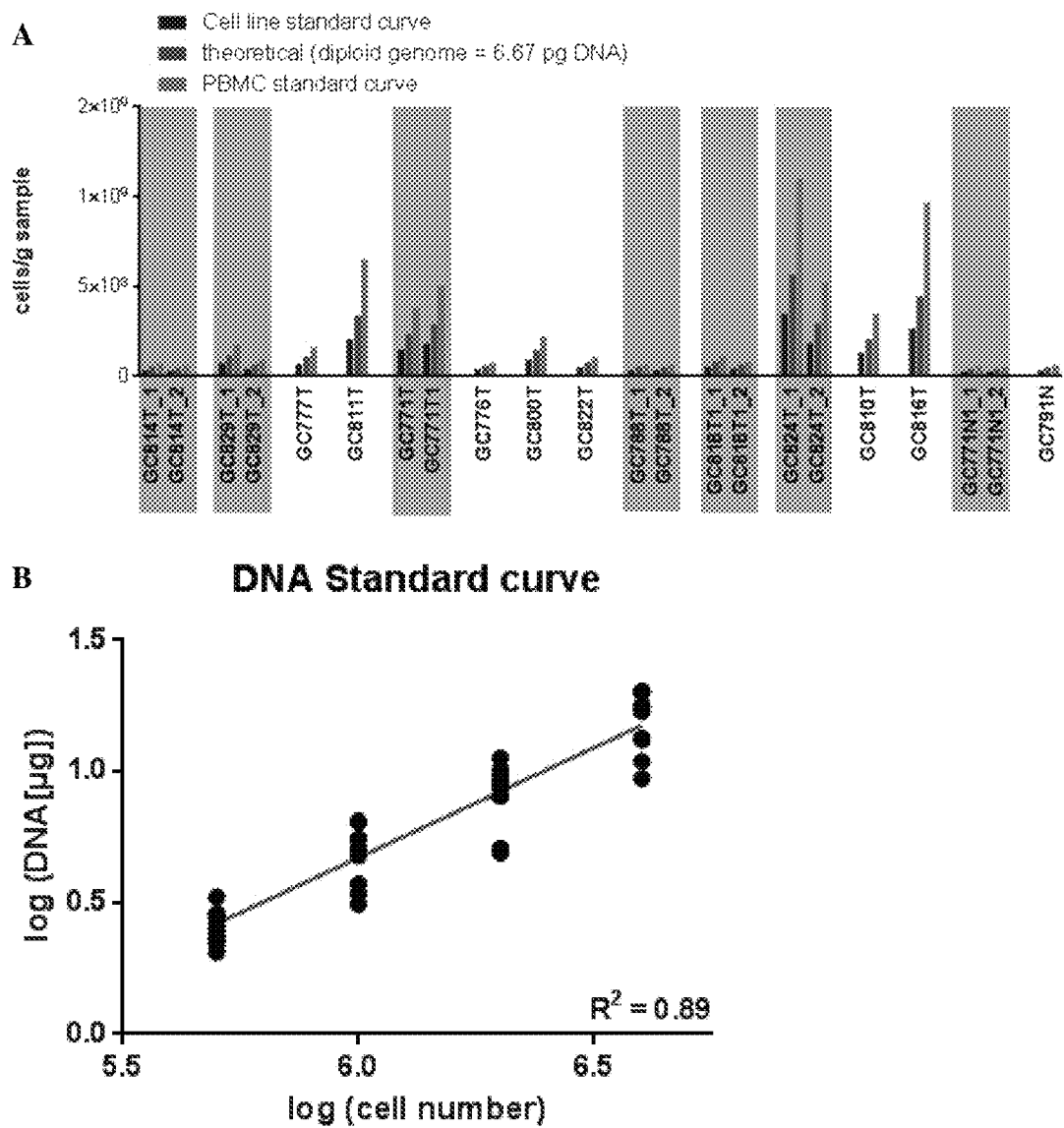

FIG. 10: shows evaluation methods of DNA content analysis. A. Comparison of three different methods for interpolation of a cell count from a given DNA amount: using a standard curve prepared from tumor cell lines (dark gray), from PBMC of healthy donors (gray), and using the theoretical weight of a human diploid genome (light gray). Biological replicates, i.e. independent tissue lysate preparations from different pieces of the same tumor, highlighted in grey. B. Plot of the PBMC standard curve, which was used to determine the total cell count of tissue samples analyzed in absolute TUMAP quantitation.

Figure 11:
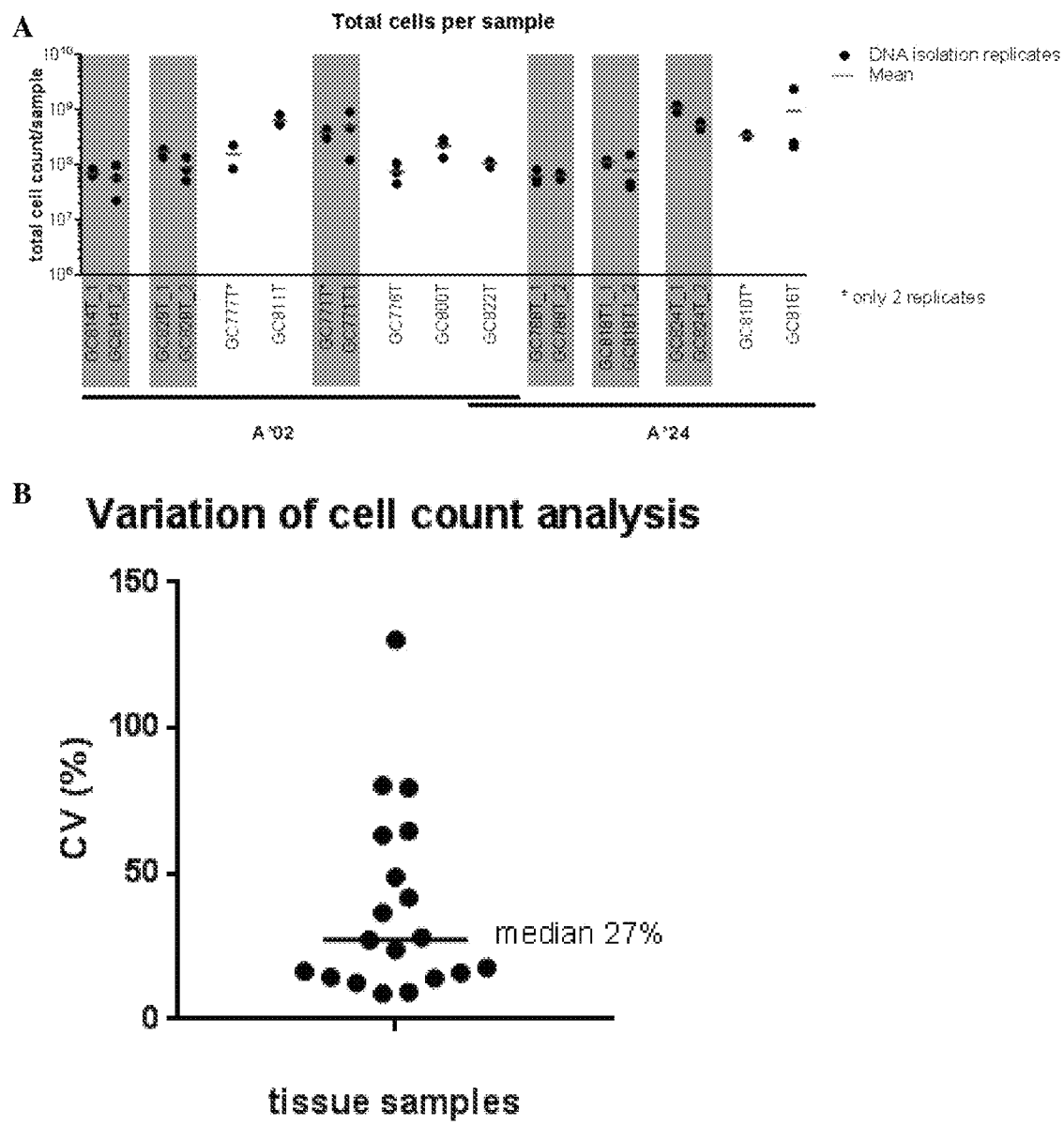

FIG. 11 shows the determination of cell count from solid, frozen tissue samples. Cell count analysis of A*02- and A*24-positive tumor samples (A) and estimated variation of cell count analysis (B). Biological replicates are highlighted in grey.

Figure 12:
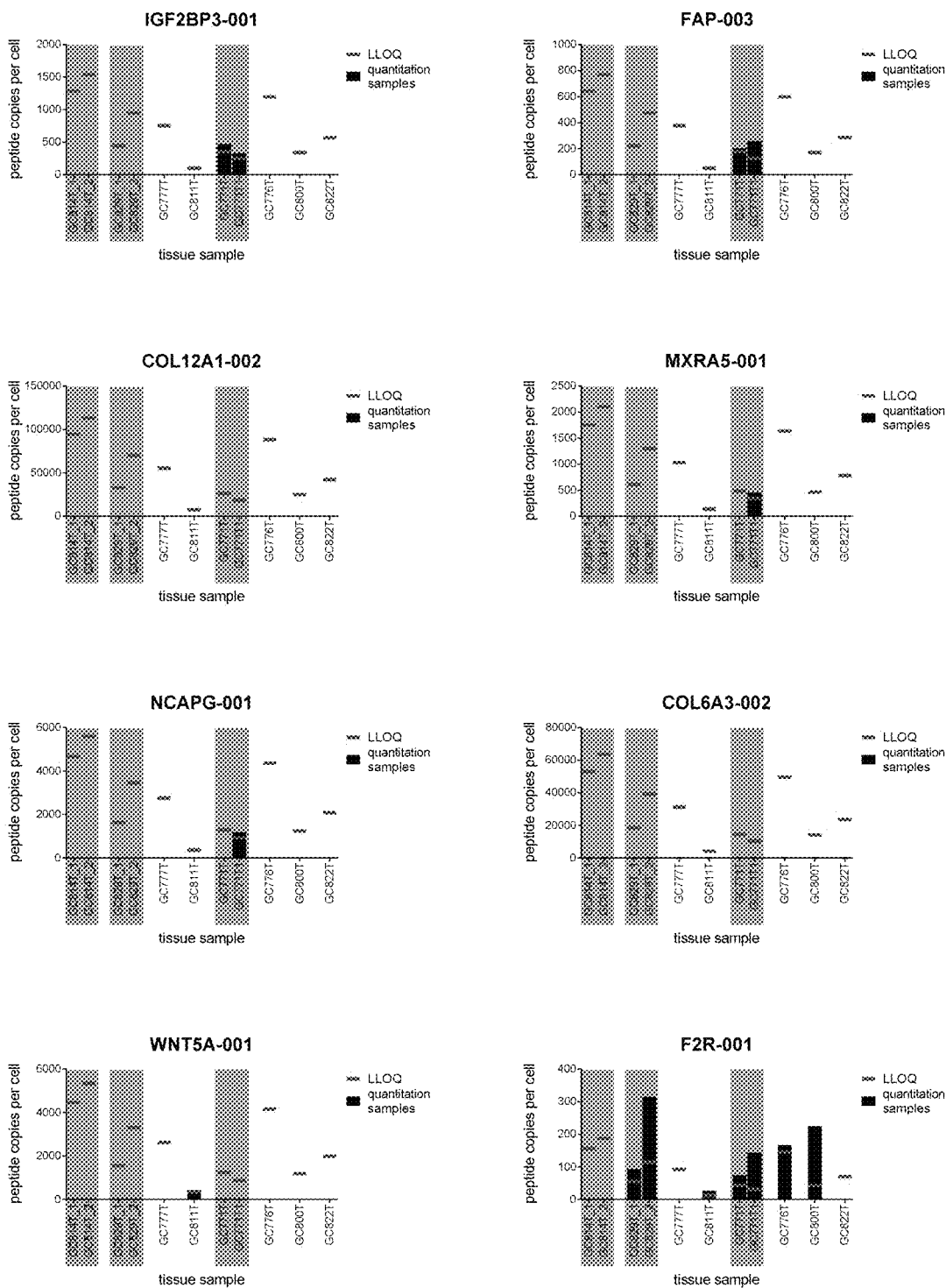

FIG. 12 shows results for peptide copies per cell for HLA-A*02 TUMAPs. Eight different GC tumors were analyzed, three of them in duplicates (biological duplicates are grouped and highlighted in gray). The LLOQ refers to the quantitation range in one MS experiment and is extrapolated to a sample- and TUMAP-specific LLOQ, i.e. the lowest copy number quantifiable in a specific sample for a specific TUMAP (depicted in gray).

Figure 13:
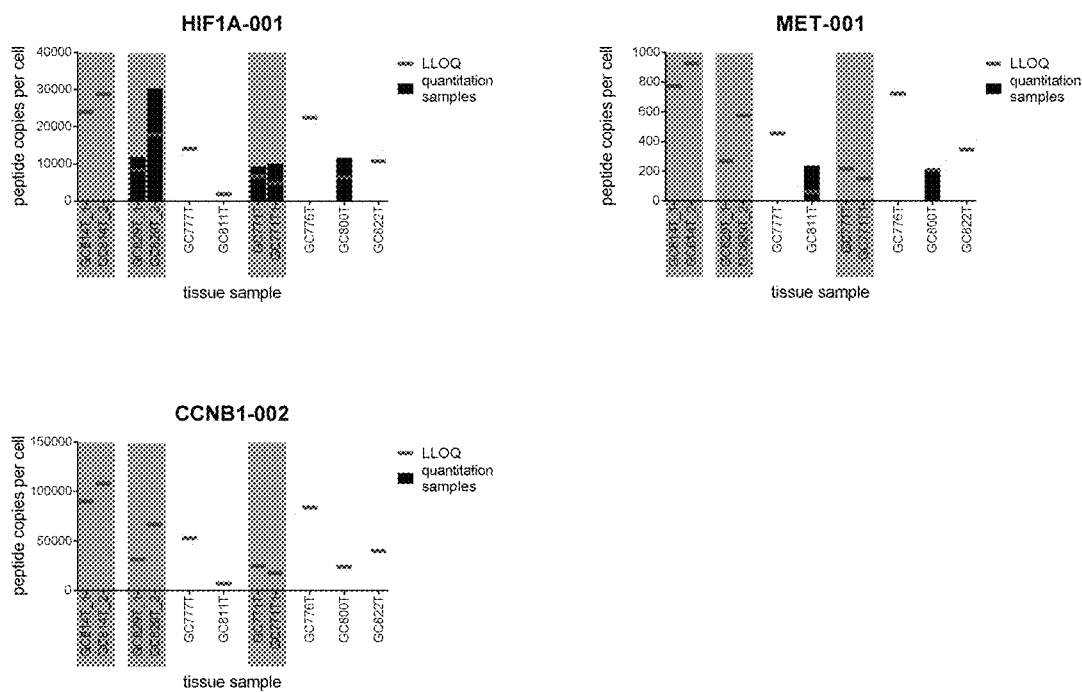

FIG. 13 shows additional results for peptide copies per cell for HLA-A*02 TUMAPs. Eight different GC tumors were analyzed, three of them in duplicates (biological duplicates are grouped and highlighted in grey). The LLOQ refers to the quantitation range in one MS experiment and is extrapolated to a sample- and TUMAP-specific LLOQ, i.e. the lowest copy number quantifiable in a specific sample for a specific TUMAP (depicted in gray).

Figure 14:
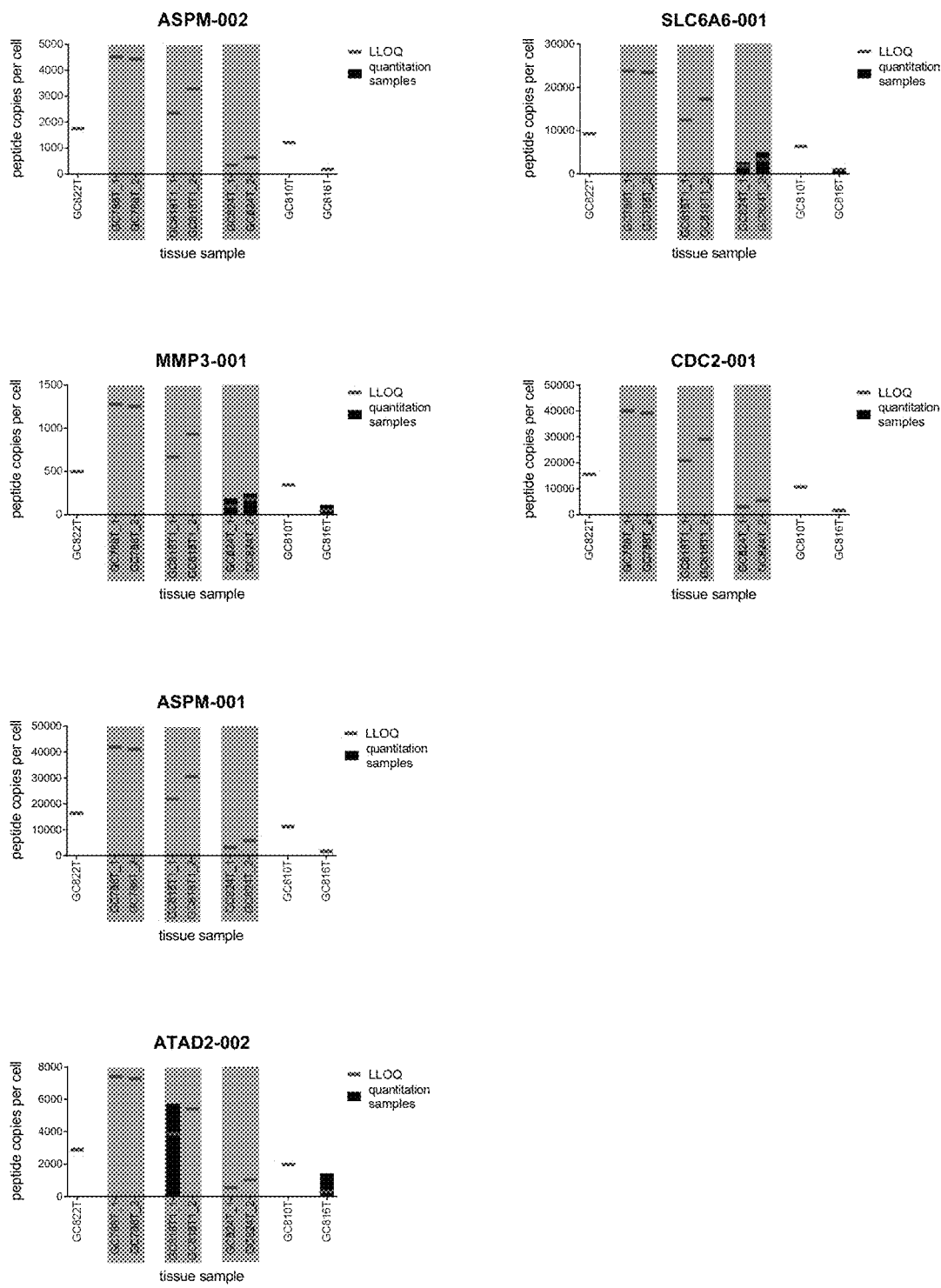

FIG. 14 shows results for peptide copies per cell for HLA-A*24 TUMAPs. Six different GC tumors were analyzed, three of them in duplicates (biological duplicates are grouped and highlighted in grey). The LLOQ refers to the quantitation range in one MS experiment and is extrapolated to a sample- and TUMAP-specific LLOQ, i.e. the lowest copy number quantifiable in a specific sample for a specific TUMAP (depicted in gray).

Figure 15:
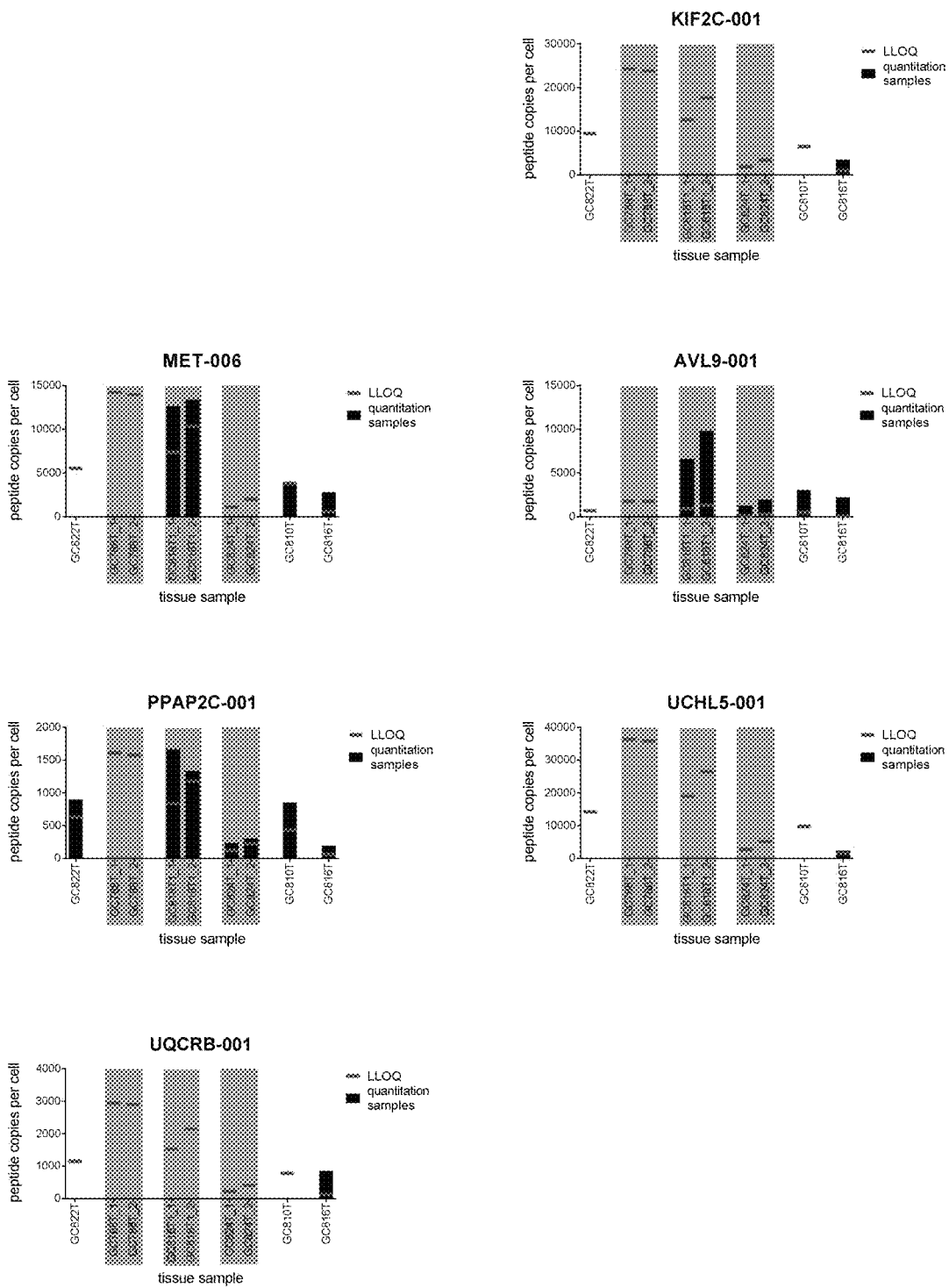

FIG. 15 shows additional results for peptide copies per cell for HLA-A*24 TUMAPs. Six different GC tumors were analyzed, three of them in duplicates (biological duplicates are grouped and highlighted in grey). The LLOQ refers to the quantitation range in one MS experiment and is extrapolated to a sample- and TUMAP-specific LLOQ, i.e. the lowest copy number quantifiable in a specific sample for a specific TUMAP (depicted in gray).

Figure 16:
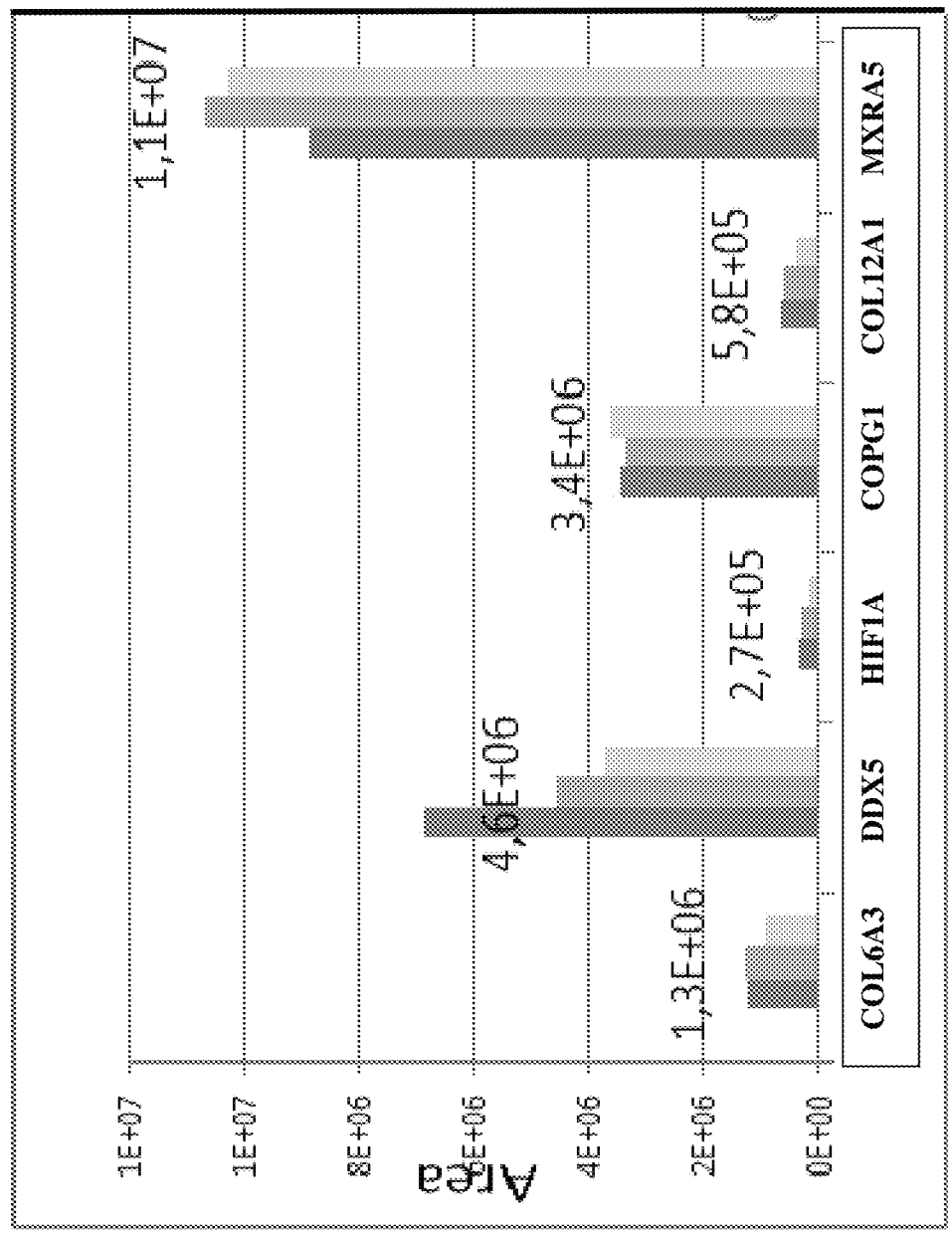

FIG. 16 shows the testing of an influence of a spiking of samples using 500 fmol of free peptides in the MHC/peptide monomer preparation. Free peptide in the analysis does not have a substantial influence for the peptides as indicated.

Figure 17:
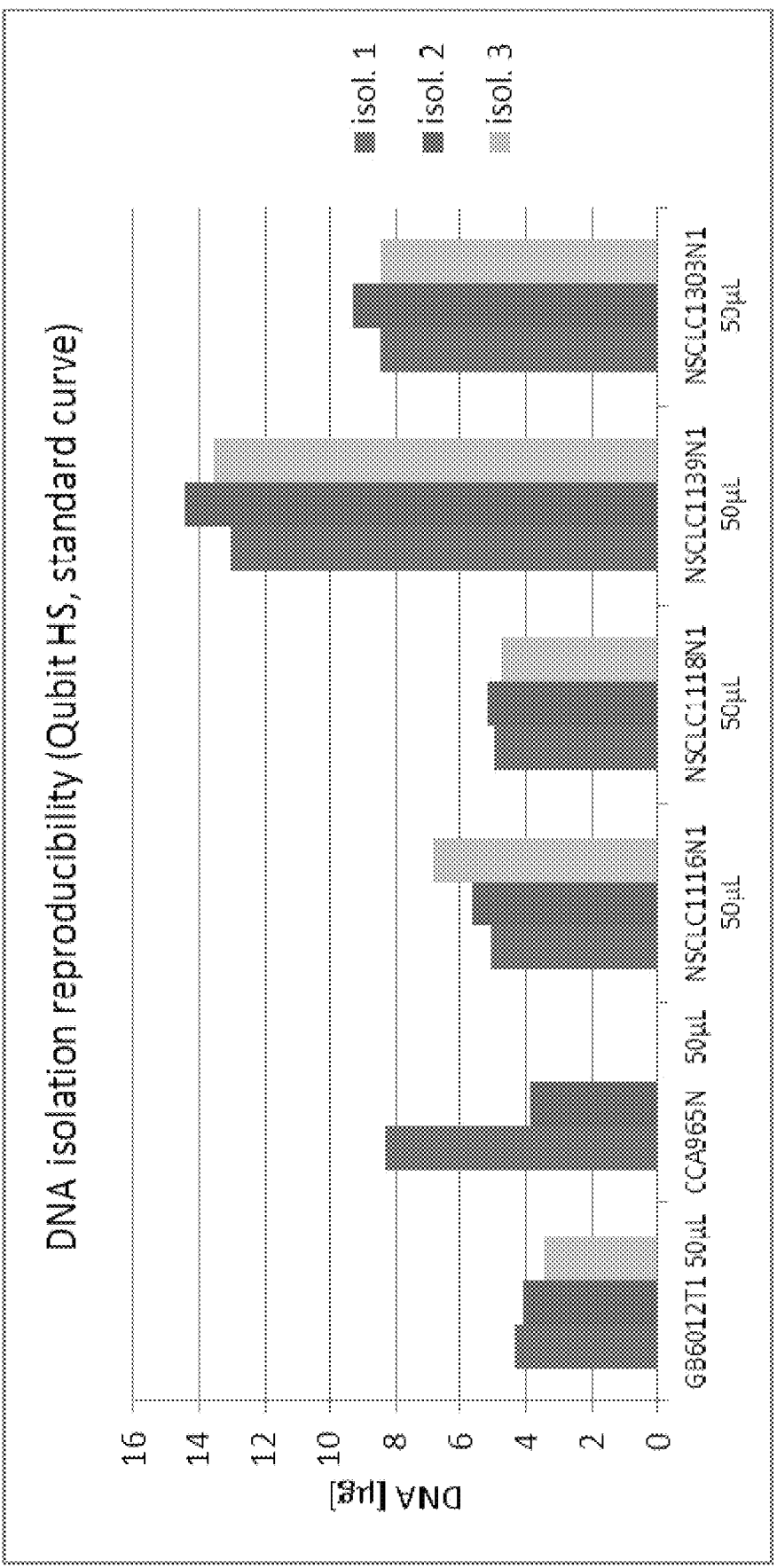

FIG. 17 shows the results of tests for the DNA isolation reproducibility using Qubit HS (fluorescence) vs. a standard curve. The samples (cancer samples, such as NSCLC) show a sufficient homogeneity. DNA was isolated from 3×50 μl aliquots.

SEQ ID No. 1 to 24 show the peptides of tables 1 and 2 that were selected for absolute quantitation according to the examples.

EXAMPLES

The following examples describe the inventive method in the context of TAAs/cancer. The invention is not restricted to the examples, as they are only one preferred embodiment of the invention. For the purposes of the present invention, all references as cited herein are incorporated by reference in their entireties.

.TABLE 1

| HLA-A*02 TUMAPs selected for absolute quantitation | | |
|---|---|---|
| No | Peptide Code | Sequence |
| 1 | IGF2BP3-001 | KIQEILTQV |
| 2 | FAP-003 | YVYQNNIYL |
| 3 | COL12A1-002 | FLVDGSWSV |
| 4 | MXRA5-001 | TLSSIKVEV |
| 5 | NCAPG-001 | YLLSYIQSI |
| 6 | COL6A3-002 | FLLDGSANV |
| 7 | WNT5A-001 | AMSSKFFLV |
| 8 | F2R-001 | TLDPRSFLL |
| 9 | HIF1A-001 | ALDGFVMVL |
| 10 | MET-001 | YVDPVITSI |
| 11 | CCNB1-002 | ILIDWLVQV |

Eleven peptides were selected for absolute quantitation.

TABLE 2

HLA-A*24 TUMAPs selected for absolute quantitation

| No | Peptide Code | Sequence |
|---|---|---|
| 12 | ASPM-002 | SYNPLWLRI |
| 13 | SLC6A6-001 | VYPNWAIGL |
| 14 | MMP3-001 | VFIFKGNQF |
| 15 | CDC2-001 | LYQILQGIVF |
| 16 | PLK4-001 | QYASRFVQL |
| 17 | ASPM-001 | RYLWATVTI |
| 18 | ATAD2-002 | KYLTVKDYL |
| 19 | KIF2C-001 | IYNGKLFDLL |
| 20 | MET-006 | SYIDVLPEF |
| 21 | AVL9-001 | FYISPVNKL |
| 22 | PPAP2C-001 | AYLVYTDRL |
| 23 | UCHL5-001 | NYLPFIMEL |
| 24 | UQCRB-001 | YYNAAGFNKL |

Fourteen peptides were selected for absolute quantitation.
The properties of one peptide (PLK4-001) turned out to be not suitable for further experiments.
For the remaining 13 peptides, absolute quantitation experiments were completed.

The quantitation of TUMAP copies per cell in solid tumor samples requires the (sub-) quantitation of
a) the isolated TUMAP,
b) the loss of the TUMAP during isolation, and
c) the cell count of the tissue sample analyzed.

An overview on the experimental approach according to the present invention is given in FIG. 1.

Peptide Quantitation by NanoLC-MS/MS

For an accurate quantitation of peptides by mass spectrometry, basic knowledge about the peptide-specific correlation of peptide quantity and MS signal needs to be learned first. As an example, the MS measurement of a peptide mixture with 10 fmol per peptide reveals that there are large peptide-specific differences in the MS signal (FIG. 2). This also implies that the range, in which a peptide may be reliably quantified by MS, depends on the individual peptide characteristics.

In addition, a linear correlation between the amount of a specific peptide and the MS signal can only be expected within a certain range. The inventors therefore decided to determine an individual calibration curve for each peptide. The range of each calibration curve was selected to reflect not only the individual quantitation range of the peptide, but also the range of MS signals for each peptide in previously analyzed tumor samples. The goal was that each calibration curve should comprise the peptide-specific MS signal range of at least 80% of our routine samples.

The generation of exact calibration curves requires a synthetic standard, which has to be quantified with an independent method and has the same characteristics as the natural TUMAP. The inventors used double isotope-labeled versions of the TUMAPs, i.e. two isotope-labeled amino acids were included during TUMAP synthesis. The double-labeled versions can be distinguished from the natural TUMAP by a mass difference of 12-18 Dalton depending on the labeled amino acid. Apart from the mass, isotope labeling does not alter the properties of the peptide in MS, i.e. peptides with the same sequence result but different isotope labels result in the same MS signal intensities (Anderson et al., 2012). After synthesis, the double-labeled TUMAPs were precisely quantified by nitrogen analysis to allow an exact correlation of peptide quantity and MS signal.

The calibration curves were prepared in at least three different matrices, i.e. HLA peptide eluates from natural samples similar to the routine MS samples, and each preparation was measured in duplicate MS runs. In order to compensate for any technical variations between MS runs, an internal standard peptide was included in all measurements. The ratio of the MS signals of the titrated peptide to the fixed internal standard was plotted, and the calibration curve was calculated by logistic regression (FIG. 3). The lower limit of quantitation (LLOQ) was visually determined considering the deviation from linearity. If deviation from linearity was not obvious, such as for peptide FAP-003 (FIG. 4), the mean ratio of the lowest peptide quantity was used to calculate the LLOQ. The upper limit of quantitation, i.e. deviation from linearity at higher concentrations, was not reached for any calibration curve.

In actual quantitation experiments, the same quantity of the internal standard was added to each sample as for the generation of the calibration curve, and the ratio of the natural to the internal standard peptide was calculated. This "internal standard method" is a common method in MS-based protein quantitation, e.g. for biomarker analysis in biological samples (Sturm et al., 2012; Prasad and Unadkat, 2014; Sato et al., 2012). The calibration curves and the values measured in actual tumor samples are shown in FIG. 4 and FIG. 5 for HLA-A*02 and in FIG. 6 and FIG. 7 for HLA-A*24 for all TUMAPs selected for absolute quantitation.

In order to estimate the variation of quantitative MS measurements, the coefficient of variation (CV in %) of the peptide content for each MS sample was calculated. The CVs per MS sample were plotted and the overall variation of MS measurements was estimated as the median CV (FIG. 8).

Efficiency of Peptide/MHC Isolation

As for any protein purification process, the isolation of proteins from tissue samples is associated with a certain loss of the protein of interest. To determine the efficiency of TUMAP isolation, peptideMHC complexes were generated for all TUMAPs selected for absolute quantitation. To be able to discriminate the spiked from the natural peptideMHC complexes, single-isotope-labeled versions of the TUMAPs were used, i.e. one isotope-labeled amino acid was introduced during TUMAP synthesis. These complexes were spiked into the freshly prepared tissue lysates, i.e. at the earliest possible point of the TUMAP isolation procedure, and then captured like the natural peptideMHC complexes in the following affinity purification. Measuring the recovery of the single-labeled TUMAPs therefore allows conclusions regarding the efficiency of isolation of individual natural TUMAPs.

The efficiency of isolation was determined in 13 samples that had been selected for absolute TUMAP quantitation (7 HLA-A*02-positive, 5 HLA-A*24-positive, and 1 HLA-A*02/A*24 double-positive sample). Eight A*02-positive samples were analyzed for isolation efficiency of A*02 TUMAPs and six A*24-positive samples for A*24 TUMAPs (FIG. 9A, B). The results suggest that for most peptides the isolation efficiency is comparable among different tissue samples. In contrast, the isolation efficiency differs between individual peptides. This suggests that the isolation efficiency, although determined in only a limited number of tissue samples, may be extrapolated to any other tissue preparation. However, it is necessary to analyze each TUMAP individually as the isolation efficiency may not be extrapolated from one peptide to others.

In few cases, the efficiency of isolation is unrealistically high and/or varies strongly, e.g. for peptide NCAPG-001 (FIG. 9A). In cases in which the efficiency could not be determined e.g. due to peptide-dependent difficulties with quantitation (e.g. high LLOQ level for peptides CCNB1-002, ASPM-001) or an efficiency higher than 100% was calculated, the inventors assumed an isolation efficiency of 100%. This is a conservative approach which most likely overestimates the efficiency of isolation and thereby ultimately leads to an underestimation of peptide copies per cell.

To estimate the variation in the efficiency of TUMAP isolation, the coefficient of variation (CV in %) for the isolation of individual TUMAPs from 6-8 samples was plotted (FIG. 9 C). Overall, the mean variation for A*02 TUMAPs is 24% and for A*24 TUMAPs 32%, respectively.

Determination of the Cell Count in Solid, Frozen Tissue

Another critical factor for calculating the number of peptide copies per cell is the estimation of the total cell count of the tissue samples used for TUMAP isolation. The inventors decided to use DNA content analysis, as this method is applicable to a wide range of samples of different origin and, most importantly, frozen samples (Forsey and Chaudhuri, 2009; Alcoser et al., 2011; Alcoser et al., 2011; Silva et al., 2013).

Considering intra-tumor heterogeneity, it is necessary to determine the cell count from a tissue fraction which is representative for the complete tissue sample used for TUMAP isolation. The tissue lysate prepared during TUMAP isolation is a suitable sample for DNA analysis, as it is more homogenous as compared to a fraction of the solid tissue. After DNA isolation, the total DNA concentration was quantified in a fluorescence-based assay (Life Technologies, Qubit HS DNA Assay), and the total DNA content of the samples was calculated.

For the calculation of cell numbers from a given DNA quantity, the inventors considered two different methods: First, the cell number may be calculated using the theoretical mass of a human genome, which has been estimated to be approximately 6.67 pg DNA per diploid genome (Alcoser et al., 2011; Konigshoff et al., 2003). Alternatively, samples with known cell number may be used to prepare a DNA standard curve with the same methods as used for the tissue samples. This method already compensates for any impact of the DNA isolation and quantitation procedure, thus improving the accuracy of our results. The inventors prepared two different standard curves, one from seven different tumor cell lines and the other from peripheral blood mononuclear cells (PBMCs) of six different healthy donors.

To compare all three evaluation methods (theoretical DNA mass and two different cell-based standard curves), the number of cells per 1 g tissue was calculated for several samples (FIG. 10A). Calculations using the cell line standard result in substantially lower cell counts (max. 3.6-fold underestimation) as compared to using the PBMC standard. This was expected considering that tumor cell lines tend to have higher portions of aneuploid cells with a higher DNA content as compared to healthy diploid PBMCs. In the literature, the proportion of diploid gastric tumors varies from 25-67% depending on the study (Hiyama et al., 1995; Tamura et al., 1991; Wiksten et al., 2008; Zhang et al., 2005; Sugai et al., 2005). As the ploidy and the fraction of aneuploid cells of the tissue samples are unknown, both standard curves may only give an estimate on the true cell count but not consider all properties of an individual tissue sample. Another source of variation is the unknown proliferation state of the tissue sample or the presence of necrotic cells. Particularly the doubling of DNA content in proliferating cells increases the quantity of DNA relative to the cell number and will thus bias cell count calculation. In two normal gastric tissue samples, the inventors calculated a lower number of cells per 1 g tissue as compared to the tumor samples with all three approaches.

As a conservative approach, the inventors decided to use the PBMC standard curve (FIG. 10 B), which may lead to an overestimation of the cell count in the portion of hyperdiploid tissue samples, leading to an underestimation of peptide copies per cell in such samples, but should never overestimate peptide copies per cell in any sample.

For the analysis of the tissue samples selected for absolute TUMAP quantitation, the inventors isolated DNA from 2-3 aliquots of tissue lysate, and each DNA preparation was quantified in 2-3 replicates in the fluorescence-based assay. The total cell count and the cell count per 1 g tissue were calculated from the total DNA content using the PBMC standard curve (FIG. 11 A). In order to obtain an estimate of the overall variation of cell count analysis, the coefficient of variation (%) was first determined at the level of each sample or, if available, biological replicate (i.e. independent tissue lysate preparations from different pieces of the same tumor). This calculation was taking into account variation between the aliquots of tissue lysate as well as replicate measurements in the fluorescence assay. These CVs are shown in FIG. 11 B, and the overall variation was determined as the median of the depicted CVs. The variability may partially be explained by the fact that the tissue lysates are not entirely homogenized, i.e. remaining tissue particles containing undissociated cells result in a higher cell count for individual isolation replicates (see e.g. GC816T in FIG. 11A).

Peptide Copies Per Cell

With data for peptide quantitation in nanoLC-MS/MS runs ("total peptide"), efficiency of TUMAP isolation ("% isolation efficiency"), and cell count of each tumor sample available, it is possible to calculate the number of TUMAP copies per cell according to the following formula:

The quantity of total peptide is calculated from the result of 2-4 nanoLC-MS/MS experiments ("peptide/run [fmol]") using the calibration curves shown in FIG. 4 to FIG. 7.

$$\text{total peptide} = \frac{\left(\frac{\text{peptide}}{\text{run}}[\text{fmol}]\right) \times \frac{6{,}022 \times 10^{23}\left[\frac{1}{\text{mol}}\right]}{10^{15}\left[\frac{\text{fmol}}{\text{mol}}\right]} \times \frac{\text{peptide eluate }[\mu L]}{MS \text{ sample per run }[\mu L]} \times 100\%}{\% \text{ of lysate used for } TUMAP \text{ isolation}} \quad (2)$$

Only MS measurements above the LLOQ, as defined using the calibration curves, are used for calculation of absolute peptide copy numbers. This LLOQ refers to the TUMAP quantity in a nanoLC-MS/MS experiment ("LLOQ/run [fmol]").

The copy number per cell over all peptides, which could be quantified, ranges from 50 to 30000 copies per cell (see Table 3).

TABLE 3

Overview on the copy numbers per cell of HLA-A*02 and HLA-A*24 TUMAPs
HLA-A*02 TUMAPs were analyzed in eight samples,
HLA-A*24 TUMAPs in six samples.

| HLA-Allele | Peptide code | Quantified in n samples (% of analyzed samples) | Copies per cell (range of individual samples and biological replicates) |
|---|---|---|---|
| A*02 | IGF2BP3-001 | 1 (13%) | 350-450 |
| A*02 | FAP-003 | 1 (13%) | 200-250 |
| A*02 | COL12A1-002 | 0 (0%) | Nq |
| A*02 | MXRA5-001 | 1 (13%) | 450 |
| A*02 | NCAPG-001 | 1 (13%) | 1000 |
| A*02 | COL6A3-002 | 0 (0%) | Nq |
| A*02 | WNT5A-001 | 1 (13%) | 400 |
| A*02 | F2R-001 | 5 (63%) | 50-300 |
| A*02 | HIF1A-001 | 3 (38%) | 9000-30000 |
| A*02 | MET-001 | 2 (25%) | 200-250 |
| A*02 | CCNB1-002 | 0 (0%) | Nq |
| A*24 | ASPM-002 | 0 (0%) | Nq |
| A*24 | SLC6A6-001 | 2 (33%) | 1000-5000 |
| A*24 | MMP3-001 | 2 (33%) | 100-250 |
| A*24 | CDC2-001 | 0 (0%) | Nq |
| A*24 | ASPM-001 | 0 (0%) | Nq |
| A*24 | ATAD2-001 | 2 (33%) | 1500-6000 |
| A*24 | KIF2C-001 | 1 (17%) | 3500 |
| A*24 | MET-006 | 3 (50%) | 2500-13500 |
| A*24 | AVL9-001 | 4 (67%) | 1000-10000 |
| A*24 | PPAP2C-001 | 5 (83%) | 200-1500 |
| A*24 | UCHL5-001 | 1 (17%) | 2500 |
| A*24 | UQCRB-001 | 1 (17%) | 900 | nq = not quantified as peptide quantity was below LLOQ

In order to visualize the LLOQ in the context of "peptide copies per cell", the "LLOQ per cell" was calculated for each TUMAP in each sample using the two formulas shown above. As the samples differ in the total cell count, the LLOQ per cell is different for each sample (see FIG. 12 and FIG. 13 for A*02 TUMAPs and FIG. 14 and FIG. 15 for A*24 TUMAPs).

Estimation of Error in Absolute TUMAP Quantitation

In order to estimate the variation in absolute TUMAP quantitation, the inventors considered the relative variation of the three major experimental results as described above:

a) the quantity of isolated TUMAP: relative deviation 1.8% (A*02) and 2.1% (A*24)
b) the efficiency of TUMAP isolation: relative deviation 24% (A*02) and 32% (A*24)
c) the cell count of the tissue sample: relative deviation 27%

Assuming normal distribution of the variable values, the relative error ($\sigma$) of "copies per cell" may be calculated as the square root of the sum of the quadratic relative error of each variable:

$$\sigma_{copies} = \sqrt{(\sigma_{total\ cell\ count})^2 + (\sigma_{total\ peptide})^2 + (\sigma_{isolation\ efficiency})^2}$$

With the values given above, the coefficient of variation for absolute peptide copy numbers per cell is about 36% for HLA-A*02 peptides, and 42% for HLA-A*24 peptides. To give an impression on the variation of the results, the absolute and relative error of peptide copies per cell for a model peptide and sample was calculated (Table 4).

TABLE 4

Exemplary calculation of the absolute and relative error in absolute TUMAP quantitation for a model peptide

| | | A*02 | | A*24 | |
|---|---|---|---|---|---|
| | value | rel. error (%) | abs. error | rel. error (%) | abs. error |
| Total cell count/sample | $1 \times 10^8$ | 27% | — | 27% | — |
| Total peptide [fmol] | 16.25 | 1.8% | — | 2.1% | — |
| Efficiency of peptideMHC isolation | 10% | 24% | — | 32% | — |
| Peptide copies per cell | 1000 | 36% | 360 | 42% | 420 |

This model calculation suggests that for the complex multi-step analysis of absolute quantitation, the variation of results is still in an acceptable range. For individual TUMAPs, the relative error may deviate from the averaged error calculated here. TUMAP copy numbers per cell may be quantitatively compared among different TUMAPs, allowing prioritizing TUMAPs to choose suitable antibody and/or soluble T cell receptor targets.

Comparison of the TUMAP Quantitation Method to Known Published Methods

An accurate approach for the absolute quantitation of MHC-associated peptide copy numbers per cell has not previously been shown. Most importantly, previously published methods for the quantitation of MHC-bound peptides using MS analysis did not consider the loss of antigen during sample preparation (Tan et al., 2011; Hogan et al., 2005). The group of Peter A. von Velen recently published a method for the "accurate quantitation of MHC-bound peptides" (Hassan et al., 2014). In this technical note, an approach was used to quantify two minor histocompatibility antigens, LB-NISCH-1A and LB-SSR1-1S, on EBV-LCL JYpp65 cells. However, the individual experimental steps differ substantially, which is summarized in the table below:

TABLE 5

Comparison of the methods for TUMAPs quantitation of Hassan et al., and the present invention

| | Hassan et al. | present invention |
|---|---|---|
| Peptide calibration curves | Used only to determine the linear range, assuming all peptides share the same correlation of peptide quantity and MS signal (slope = 1) | To determine the linear range, the LLOQ and to quantify peptides; considers peptide-specific correlation of quantity and MS signal for each individual peptide |
| Peptide quantitation | One point calibration: signal ratio to spiked standard peptide | Internal standard method, based on peptide-specific calibration curve, quantitation of samples near the LLOQ |
| Efficiency of isolation | peptideMHC complexes spiked in lysate after 2 hour lysis and clearance by centrifugation, disregards peptide loss in these steps | peptideMHC complexes spiked directly after tissue homogenization, i.e. the earliest point in peptide isolation |
| Samples | Cell line | Solid tumor tissue |
| Sample preparation | Additional C18 chromatography step prior to the final nanoLC-MS/MS, used to reduce sample complexity. | Immediate usage of a immunoprecipitated and filtered sample for nanoLC-MS/MS |

TABLE 5-continued

Comparison of the methods for TUMAPs quantitation of Hassan et al., and the present invention

| | Hassan et al. | present invention |
|---|---|---|
| Determination of cell number | Counting of cells during cell pellet preparation | DNA content analysis from lysate of solid tissues |
| Error calculation | Consider only variation of MS replicates (CV 0.1-7.1%), but not the variation of peptideMHC isolation efficiency (26% and 91% respectively), and of the cell count. | Variations in MS replicates (CV on average 1.8-2.1%), peptideMHC isolation efficiency (CV on average 24-32%), and cell count determination (CV on average 27%) are considered. |

The copy numbers of the two peptides analyzed by Hassan et al. varied from 800 to 5300 (relative deviation 74%), and 3000 to 12000 (relative deviation 60%) copies per cell among the biological replicates, respectively. The reason for this variation was not clearly discussed, but may be due to the usage of different MS instruments.

In summary, the more refined method of the present invention is expected to contribute to more accurate and reliable results.

Quantification of Peptides Having Low Copy Numbers

In order to show the power of the inventive method, the data as presented in the following table was generated. Peptides were identified that are present in only very small copy numbers, amongst them peptide PDE11-001. It can be seen that the method allows the determination of as few as about 10 copies of the peptide per cell.

TABLE 6

Quantification of peptides having low copy numbers

| | Copies per cell | | | Number of samples | | | |
|---|---|---|---|---|---|---|---|
| Peptide Code | Min | Median | Max | >LLOQ | >LOD | evaluable | Source/HLA |
| Peptide 1 | 20 | 20 | 20 | 1 | 5 | 16 | NSCLC/A*02 |
| Peptide 2 | 10 | 30 | 300 | 13 | 16 | 17 | NSCLC/A*02 |
| Peptide 3 | 10 | 30 | 50 | 4 | 10 | 18 | NSCLC/A*02 |
| Peptide 4 | 10 | 30 | 100 | 17 | 17 | 19 | NSCLC/A*02 |
| Peptide 5 | 20 | 20 | 90 | 7 | 8 | 11 | NSCLC/A*02 |
| Peptide 6 | 10 | 20 | 50 | 6 | 6 | 10 | NSCLC/A*02 |
| Peptide 7 | <10 | 30 | 200 | 9 | 12 | 15 | PC/A*02 |
| PDE11-001 | <10 | 10 | 30 | 8 | 9 | 10 | PC/A*02 |

PC—prostate cancer—Sequence PDE11-001 is ALLESRVNL (SEQ ID No. 25)

PDE11-001 is an HLA-A*02 binding peptide derived from phosphodiesterase 11A (PDE11A), which catalyzes the hydrolysis of cAMP and cGMP, thus downregulating the respective signalling pathways. Mutations in PDE11A have been associated with adrenocortical hyperplasia as well as with familial testicular germ cell tumors. The peptide was detected on prostate cancer samples, and also in hepatocellular, pancreatic and renal cell carcinoma and not on any normal tissues.

REFERENCES AS CITED

Alcoser S Y, Kimmel D J, Borgel S D, Carter J P, Dougherty K M, Hollingshead M G (2011). Real-time PCR-based assay to quantify the relative amount of human and mouse tissue present in tumor xenografts. BMC. Biotechnol. 11, 124.

Anderson N L, Razavi M, Pearson T W, Kruppa G, Paape R, Suckau D (2012). Precision of heavy-light peptide ratios measured by maldi-tof mass spectrometry. J Proteome. Res 11, 1868-1878.

Forsey R W, Chaudhuri J B (2009). Validity of DNA analysis to determine cell numbers in tissue engineering scaffolds. Biotechnol. Lett. 31, 819-823.

Hassan C, Kester M G, Oudgenoeg G, de Ru A H, Janssen G M, Drijfhout J W, Spaapen R M, Jimenez C R, Heemskerk M H, Falkenburg J H, van Veelen P A (2014). Accurate quantitation of MHC-bound peptides by application of isotopically labeled peptide MHC complexes. J Proteomics.

Hiyama E, Yokoyama T, Tatsumoto N, Hiyama K, Imamura Y, Murakami Y, Kodama T, Piatyszek M A, Shay J W, Matsuura Y (1995). Telomerase activity in gastric cancer. Cancer Res 55, 3258-3262.

Hogan K T, Sutton J N, Chu K U, Busby J A, Shabanowitz J, Hunt D F, Slingluff C L, Jr. (2005). Use of selected reaction monitoring mass spectrometry for the detection of specific MHC class I peptide antigens on A3 supertype family members. Cancer Immunol. Immunother. 54, 359-371.

Konigshoff M, Wilhelm J, Bohle R M, Pingoud A, Hahn M (2003). HER-2/neu gene copy number quantified by real-time PCR: comparison of gene amplification, heterozygosity, and immunohistochemical status in breast cancer tissue. Clin Chem. 49, 219-229.

Prasad B, Unadkat J D (2014). Comparison of Heavy Labeled (SIL) Peptide versus SILAC Protein Internal Standards for L C-M S/M S Quantification of Hepatic Drug Transporters. Int. J Proteomics. 2014, 451510.

Sato Y, Miyashita A, Iwatsubo T, Usui T (2012). Simultaneous absolute protein quantification of carboxylesterases 1 and 2 in human liver tissue fractions using liquid chromatography-tandem mass spectrometry. Drug Metab Dispos. 40, 1389-1396.

Silva A L, Rosalia R A, Sazak A, Carstens M G, Ossendorp F, Oostendorp J, Jiskoot W (2013). Optimization of encapsulation of a synthetic long peptide in PLGA nanoparticles: low-burst release is crucial for efficient CD8 (+) T cell activation. Eur. J Pharm. Biopharm. 83, 338-345.

Sturm R, Sheynkman G, Booth C, Smith L M, Pedersen J A, Li L (2012). Absolute quantification of prion protein (90-231) using stable isotope-labeled chymotryptic peptide standards in a L C-MRM AQUA workflow. J Am. Soc. Mass Spectrom. 23, 1522-1533.

Sugai T, Habano W, Jiao Y F, Suzuki M, Takagane A, Nakamura S (2005). Analysis of genetic alterations associated with DNA diploidy, aneuploidy and multiploidy in gastric cancers. Oncology 68, 548-557.

Tamura G, Kihana T, Nomura K, Terada M, Sugimura T, Hirohashi S (1991). Detection of frequent p53 gene mutations in primary gastric cancer by cell sorting and polymerase chain reaction single-strand conformation polymorphism analysis. Cancer Res 51, 3056-3058.

Tan C T, Croft N P, Dudek N L, Williamson N A, Purcell A W (2011). Direct quantitation of MHC-bound peptide epitopes by selected reaction monitoring. Proteomics. 11, 2336-2340.

Wiksten J P, Lundin J, Nordling S, Kokkola A, Haglund C (2008). Comparison of the prognostic value of a panel of tissue tumor markers and established clinicopathological factors in patients with gastric cancer. Anticancer Res 28, 2279-2287.

Zhang H, Yi E C, Li X J, Mallick P, Kelly-Spratt K S, Masselon C D, Camp D G, Smith R D, Kemp C J, Aebersold R (2005). High throughput quantitative analysis of serum proteins using glycopeptide capture and liquid chromatography mass spectrometry. Mol. Cell Proteomics. 4, 144-155.

The invention claimed is:

1. A method of inducing a T cell response in an individual, comprising
obtaining a biological sample comprising target cells over-presenting, overexpressing, and/or selectively presenting at least one MHC peptide ligand on the cell surface from the individual,
quantifying the copy number of the at least one MHC peptide ligand per target cell from the sample,
wherein the quantifying comprises
a) preparing a cell lysate from the target cells over-presenting, overexpressing, and/or selectively presenting said at least one MHC peptide ligand from the biological sample to obtain a preparation A,
b) determining a cell count of said preparation A,
c) adding a pre-determined amount of said at least one MHC peptide ligand labelled with a first isotope in an MHC complex to be quantified to said preparation A ("spiking I") to obtain a preparation B,
d) isolating the at least one MHC peptide ligand and the at least one MHC peptide ligand labelled with a first isotope from said preparation B to obtain a peptide eluate,
e) adding a pre-determined amount of the at least one MHC peptide ligand labelled with a second isotope to be quantified to said peptide eluate ("spiking II") to obtain a preparation C,
wherein the first isotope is different from the second isotope,
f) performing a mass spectrometry analysis on said at least one MHC peptide ligand in the preparation C to generate at least one
fa) signal for said at least one MHC peptide ligand labelled with the first isotope isolated from the preparation B to calculate efficiency of said isolating,
fb) signal for the pre-determined amount of said at least one MHC peptide ligand labelled with the second isotope as added to the preparation C, and fc) signal for said at least one MHC peptide ligand from said preparation A, f1) performing a mass spectrometry analysis on serially titrated amounts of said at least one MHC peptide ligand labelled with a third isotope and the pre-determined amount of said at least one MHC peptide ligand labelled with a fourth isotope as an internal standard to generate f1a) signal for the serially titrated amounts of said at least one MHC peptide ligand labelled with a third isotope, and f1b) signal for the pre-determined amount of said at least one MHC peptide ligand labelled with a fourth isotope, wherein the third isotope is different from the fourth isotope, f2) plotting a ratio of the signal of f1a)/the signal of f1b) to generate a calibration curve, wherein a lower limit of quantitation (LLOQ) is determined when the ratio of the signal of f1a)/the signal of f1b) deviates from linearity in the calibration curve, and;

g) quantifying said at least one MHC peptide ligand in the preparation A based on a comparison of the signals as obtained in f) with ga) the cell count as obtained, gb) the pre-determined amount of said at least one peptide-MHC ligand labelled with the first isotope and/or peptide-MHC ligand complex labelled with the first isotope to be quantified as added to the preparation B, and gc) the pre-determined amount of said at least one MHC peptide ligand labelled with a second isotope to be quantified as added to the preparation C, wherein the quantifying in g) comprises selecting a ratio of the signal of fc)/the signal of fb) at or above the LLOQ and calculating the copy number of the at least one MEW peptide ligand per target cell based on the selected ratio in the calibration curve, selecting the at least one MHC peptide ligand that has the calculated copy number from 10 to 30000 copies per target cell, preparing a composition comprising a T cell, wherein the T cell binds to the selected at least one MEW peptide ligand in a complex with an MHC molecule, and administering the composition to the individual.

2. The method of claim 1, wherein said at least one MEW peptide ligand is selected from a tumor associated peptide (TAA) or disease associated peptide (DAA).

3. The method of claim 1, wherein said biological sample is selected from a tissue sample, a blood sample, a tumor sample, or a sample of an infected tissue.

4. The method of claim 1, wherein the preparing a cell lysate comprises enzymatic digestion of tissues, and/or cellular lysis.

5. The method of claim 1, wherein said cell count is determined using a method selected from counting cell nuclei, photometric DNA-determination, fluorimetric DNA-determination, or quantitative PCR.

6. The method of claim 1, further comprising determining the amount of at least one type of MHC-molecule in said preparation A.

7. The method of claim 1, wherein the isolating comprises using chromatography.

8. The method of claim 1, wherein said method is capable of being performed and/or is performed on a high-throughput basis.

9. The method of claim 1, wherein said method consists of said a) to g).

10. The method of claim 1, wherein the individual is suffering from a medical condition.

11. The method of claim 10, further comprising generating a personalized MHC ligand profile or a personalized disease-specific MHC ligand profile, based on said at least one MHC peptide ligand as quantified.

12. The method of claim 1, wherein the isolating comprises using affinity chromatography.

13. The method of claim 10, further comprising generating a personalized MHC ligand profile based on said at least one MHC peptide ligand as quantified.

14. The method of claim 10, further comprising generating a personalized disease-specific MHC ligand profile based on said at least one MHC peptide ligand as quantified.

15. The method of claim 1, wherein the selecting comprises selecting the at least one MHC peptide ligand that has the calculated copy number from 50 to 30000 copies per target cell.

16. The method of claim 1, wherein the T cell response comprises a cytotoxic T cell response.

* * * * *